United States Patent
Berger et al.

(10) Patent No.: US 8,748,433 B2
(45) Date of Patent: Jun. 10, 2014

(54) β3 ADRENERGIC RECEPTOR AGONISTS

(75) Inventors: Richard Berger, Perkasie, PA (US);
Scott D. Edmondson, Clark, NJ (US);
Bart H. Harper, New York, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 36 days.

(21) Appl. No.: 13/643,361

(22) PCT Filed: Apr. 25, 2011

(86) PCT No.: PCT/US2011/033741
§ 371 (c)(1),
(2), (4) Date: Oct. 25, 2012

(87) PCT Pub. No.: WO2011/137054
PCT Pub. Date: Nov. 3, 2011

(65) Prior Publication Data
US 2013/0053403 A1    Feb. 28, 2013

Related U.S. Application Data

(60) Provisional application No. 61/330,013, filed on Apr. 30, 2010.

(51) Int. Cl.

| | | |
|---|---|---|
| *C07D 403/14* | (2006.01) | |
| *A61K 31/513* | (2006.01) | |
| *A61K 31/4184* | (2006.01) | |
| *A61K 31/497* | (2006.01) | |
| *C07D 417/14* | (2006.01) | |
| *A61K 31/427* | (2006.01) | |
| *A61K 31/4196* | (2006.01) | |
| *C07D 487/04* | (2006.01) | |
| *A61K 31/428* | (2006.01) | |
| *A61K 31/4439* | (2006.01) | |
| *C07D 401/14* | (2006.01) | |
| *A61K 31/444* | (2006.01) | |
| *A61P 13/10* | (2006.01) | |
| *A61P 13/00* | (2006.01) | |

(52) U.S. Cl.
CPC ............ *C07D 401/14* (2013.01); *C07D 403/14* (2013.01); *C07D 417/14* (2013.01); *A61K 31/4439* (2013.01); *A61K 31/4196* (2013.01); *A61K 31/4184* (2013.01); *A61K 31/427* (2013.01); *A61K 31/428* (2013.01)
USPC ...... 514/255.05; 514/274; 514/394; 514/365; 514/383; 514/269; 514/367; 514/338; 514/333; 544/316; 544/319; 544/405; 546/256; 546/269.7; 546/270.1; 546/273.4; 548/159; 548/181; 548/266.4; 548/305.1; 548/305.7; 548/306.1

(58) Field of Classification Search
CPC .. C07D 235/20; C07D 401/14; C07D 403/14; C07D 417/14; A61K 31/4439; A61K 31/4196; A61K 31/4184; A61K 31/427; A61K 31/428
USPC ............ 514/255.05, 274, 394, 365, 383, 269, 514/367, 338, 333; 544/316, 405, 319; 546/270, 269.7, 273.4, 256; 548/306.1, 548/305.7, 305.1, 181, 266.4, 159, 217–224
See application file for complete search history.

(56) References Cited

U.S. PATENT DOCUMENTS

| | | | | |
|---|---|---|---|---|
| 5,627,200 | A  * | 5/1997 | Kreutter et al. | 514/367 |
| 6,291,491 | B1 * | 9/2001 | Weber et al. | 514/357 |
| 8,399,480 | B2 * | 3/2013 | Berger et al. | 514/306 |
| 2002/0037907 | A1 * | 3/2002 | Steffan et al. | 514/317 |
| 2009/0253705 | A1 * | 10/2009 | Berger et al. | 514/248 |

OTHER PUBLICATIONS

Takasu et al., Effect of (R)-2-(2-Aminothiazol-4-yl)-4'-(2-[(2-hydroxy-2-phenylethyl)amino]ethyl), Acetanillide (YM178), a Novel Selective beta3-Adrenoceptor Agonist, on Bladder Function, JPET, 2007, vol. 321, No. 2, pp. 642-647; pp. 643, Fig. 1.

* cited by examiner

*Primary Examiner* — Samantha Shterengarts
*Assistant Examiner* — Amanda L Aguirre
(74) *Attorney, Agent, or Firm* — Patricia A. Shatynski; Valerie J. Camara

(57) ABSTRACT

The present invention provides compounds of Formula (I), pharmaceutical compositions thereof, and methods of using the same in the treatment or prevention of diseases mediated by the activation of b3-adrenoceptor.

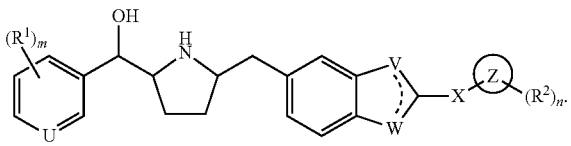

19 Claims, No Drawings

β3 ADRENERGIC RECEPTOR AGONISTS

CROSS REFERENCE TO RELATED APPLICATIONS

This application is a U.S. National Phase application under 35 U.S.C. §371 of PCT Application No. PCT/US2011/033741, filed Apr. 25, 2011 which claims priority under 35 U.S.C. §119(e) from U.S. Provisional Application Ser. No. 61/330,013, filed Apr. 30, 2010.

BACKGROUND OF THE INVENTION

The function of the lower urinary tract is to store and periodically release urine. This requires the orchestration of storage and micturition reflexes which involve a variety of afferent and efferent neural pathways, leading to modulation of central and peripheral neuroeffector mechanisms, and resultant coordinated regulation of sympathetic and parasympathetic components of the autonomic nervous system as well as somatic motor pathways. These proximally regulate the contractile state of bladder (detrusor) and urethral smooth muscle, and urethral sphincter striated muscle.

β Adrenergic receptors (βAR) are present in detrusor smooth muscle of various species, including human, rat, guinea pig, rabbit, ferret, dog, cat, pig and non-human primate. However, pharmacological studies indicate there are marked species differences in the receptor subtypes mediating relaxation of the isolated detrusor; β1AR predominate in cats and guinea pig, β2AR predominate in rabbit, and β3AR contribute or predominate in dog, rat, ferret, pig, cynomolgus and human detrusor. Expression of βAR subtypes in the human and rat detrusor has been examined by a variety of techniques, and the presence of β3AR was confirmed using in situ hybridization and/or reverse transcription-polymerase chain reaction (RT-PCR). Real time quantitative PCR analyses of β1AR, β2AR and β3AR mRNAs in bladder tissue from patients undergoing radical cystectomy revealed a preponderance of β3AR mRNA (97%, cf 1.5% for β1AR mRNA and 1.4% for β2AR mRNA). Moreover, β3AR mRNA expression was equivalent in control and obstructed human bladders. These data suggest that bladder outlet obstruction does not result in downregulation of β3AR, or in alteration of β3AR-mediated detrusor relaxation. β3AR responsiveness also has been compared in bladder strips obtained during cystectomy or enterocystoplasty from patients judged to have normal bladder function, and from patients with detrusor hyporeflexia or hyperreflexia. No differences in the extent or potency of β3AR agonist mediated relaxation were observed, consistent with the concept that the β3AR activation is an effective way of relaxing the detrusor in normal and pathogenic states.

Functional evidence in support of an important role for the β3AR in urine storage emanates from studies in vivo. Following intravenous administration to rats, the rodent selective β3AR agonist CL316243 reduces bladder pressure and in cystomeric studies increases bladder capacity leading to prolongation of micturition interval without increasing residual urine volume.

Overactive bladder is characterized by the symptoms of urinary urgency, with or without urgency urinary incontinence, usually associated with frequency and nocturia. The prevalence of OAB in the United States and Europe has been estimated at 16 to 17% in both women and men over the age of 18 years. Overactive bladder is most often classified as idiopathic, but can also be secondary to neurological condition, bladder outlet obstruction, and other causes. From a pathophysiologic perspective, the overactive bladder symptom complex, especially when associated with urge incontinence, is suggestive of detrusor overactivity. Urgency with or without incontinence has been shown to negatively impact both social and medical well-being, and represents a significant burden in terms of annual direct and indirect healthcare expenditures. Importantly, current medical therapy for urgency (with or without incontinence) is suboptimal, as many patients either do not demonstrate an adequate response to current treatments, and/or are unable to tolerate current treatments (for example, dry mouth associated with anticholinergic therapy). Therefore, there is need for new, well-tolerated therapies that effectively treat urinary frequency, urgency and incontinence, either as monotherapy or in combination with available therapies. Agents that relax bladder smooth muscle, such as β3AR agonists, are expected to be effective for treating such urinary disorders.

SUMMARY OF THE INVENTION

The present invention relates to novel compounds of Formula I or pharmaceutically acceptable salts thereof:

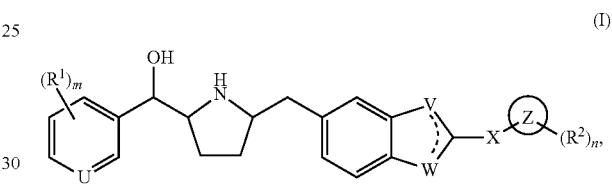

(I)

pharmaceutical compositions containing the compounds disclosed herein, as well as methods for the treatment or prophylaxis of disorders mediated through β3AR.

DESCRIPTION OF THE INVENTION

Described herein are compounds of Formula I or a pharmaceutically acceptable salt thereof:

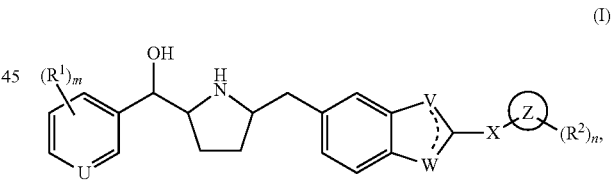

(I)

wherein the dash bond "----" means a single or double bond while conforming to the valency rule for the ring atoms;
m is 0, 1, 2, 3, 4 or 5;
n is 0, 1, 2, 3, 4 or 5;
p is 0, 1 or 2;
U is —CH= or —N=;
V is selected from the group consisting of:
  (1) —O—,
  (2) —N=, and
  (3) —NR$^3$—;
W is —N= or —NR$^3$—;
X is selected from the group consisting of:
  (1) a bond,
  (2) C$_1$-C$_5$ alkanediyl optionally substituted with 1 to 5 groups selected from:
    (a) hydroxy,
    (b) halogen, (c) —CO$_2$R$^3$,
(d) —CONR$^3$R$^3$,
(e) —NR$^3$R$^3$,
(f) —S(O)$_p$R$^3$,
(g) C$_3$-C$_8$ cycloalkyl,
(h) C$_1$-C$_{10}$ alkoxy optionally substituted with 1 to 5 halogens, and
(i) Z optionally substituted with 1 to 5 groups independently selected from hydroxyl, halogen, oxo, trifluoromethyl, trifluoromethoxy, C$_1$-C$_{10}$ alkyl and C$_1$-C$_{10}$ alkoxy;
(3) —(CH$_2$)$_n$NR$^6$(CH$_2$)$_n$—, wherein each CH$_2$ is optionally substituted with 1 to 2 R$^6$ groups; and
(4) —(CH$_2$)$_n$O(CH$_2$)$_n$—, wherein each CH$_2$ is optionally substituted with 1 to 2 R$^6$ groups;

Z is selected from the group consisting of:
(1) phenyl,
(2) 5 or 6-membered heterocyclic ring with from 1 to 4 heteroatoms independently selected from oxygen, sulfur and nitrogen,
(3) a C$_5$-C$_8$ carbocyclic ring fused to a 5 or 6-membered heterocyclic ring with from 1 to 4 heteroatoms independently selected from oxygen, sulfur and nitrogen, and
(4) 5 or 6-membered heterocyclic ring with from 1 to 4 heteroatoms independently selected from oxygen, sulfur and nitrogen fused to a 5 or 6-membered heterocyclic ring with from 1 to 4 heteroatoms independently selected from oxygen, sulfur and nitrogen;

each occurrence of R$^1$ is independently selected from the group consisting of:
(1) C$_1$-C$_{10}$ alkyl optionally substituted with up 1 to 5 groups selected from:
  (a) hydroxy,
  (b) halogen,
  (c) cyano,
  (d) C$_3$-C$_8$ cycloalkyl,
  (e) —S(O)$_p$NR$^3$R$^3$,
  (f) —NR$^3$SO$_2$R$^3$, and
  (g) Z optionally substituted with 1 to 5 groups independently selected from hydroxyl, halogen, oxo, trifluoromethyl, trifluoromethoxy, C$_1$-C$_{10}$ alkyl and C$_1$-C$_{10}$ alkoxy;
(2) C$_3$-C$_8$ cycloalkyl,
(3) oxo,
(4) halogen,
(5) cyano,
(7) —S(O)$_p$NR$^3$R$^3$,
(9) —NR$^3$SO$_2$R$^3$, and
(11) Z optionally substituted with 1 to 5 groups independently selected from hydroxyl, halogen, oxo, trifluoromethyl, trifluoromethoxy, C$_1$-C$_{10}$ alkyl and C$_1$-C$_{10}$ alkoxy;

each occurrence of R$^2$ is independently selected from the group consisting of:
(1) hydrogen,
(2) C$_1$-C$_{10}$ alkyl optionally substituted with 1 to 5 groups selected from
  (a) hydroxy,
  (b) halogen,
  (c) —CO$_2$R$^3$,
  (d) —S(O)$_p$R$^3$,
  (e) C$_3$-C$_8$ cycloalkyl,
  (1) C$_1$-C$_{10}$ alkoxy optionally substituted with 1 to 5 halogens, and
  (g) Z optionally substituted with 1 to 5 groups selected from hydroxyl, halogen, oxo, trifluoromethyl, trifluoromethoxy, C$_1$-C$_{10}$ alkyl and C$_1$-C$_{10}$ alkoxy,
(3) C$_3$-C$_8$ cycloalkyl, and
(4) Z optionally substituted with 1 to 5 groups independently selected from
  (a) halogen,
  (b) nitro,
  (e) oxo,
  (d) —NR$^3$R$^3$,
  (e) C$_1$-C$_{10}$ alkoxy optionally substituted with up to 5 halogens,
  (f) —S(O)$_p$R$^3$, and
  (g) C$_1$-C$_{10}$ alkyl optionally substituted with 1 to 5 groups selected from hydroxy, halogen, trifluoromethyl, cyano, CO$_2$R$^3$, C$_3$-C$_8$ cycloalkyl;
  (h) —S(O)$_p$NR$^3$R$^3$, and
  (i) —NR$^3$SO$_2$R$^3$;

each occurrence of R$^3$ is independently selected from the group consisting of:
(1) hydrogen, and
(2) C$_1$-C$_{10}$ alkyl optionally substituted with phenyl, halogen, cyano, and hydroxyl; and each occurrence of R$^6$ is independently selected from the group consisting of:
(1) hydrogen,
(2) C$_1$-C$_{10}$ alkyl optionally substituted with phenyl, halogen, cyano, and hydroxyl,
(3) —S(O)$_p$—C$_1$-C$_{10}$ alkyl,
(4) —CO$_2$R$^3$,
(5) —CONR$^3$R$^3$, and
(6) Z optionally substituted with 1 to 5 groups selected from hydroxyl, halogen, oxo, trifluoromethyl, trifluoromethoxy, C$_1$-C$_{10}$ alkyl and C$_1$-C$_{10}$ alkoxy.

In another embodiment, compounds disclosed herein have Formula I, wherein
m is 0, 1, 2 or 3;
n is 0, 1, 2, 3 or 4;
p is 0, 1 or 2;
U is —CH= or —N=;
V is selected from the group consisting of:
(1) —O—,
(2) —N=, and
(3) —NR$^3$—;
W is —N= or —NR$^3$—;
X is selected from the group consisting of:
(1) a bond, and
(2) C$_1$-C$_4$ alkanediyl optionally substituted with 1 to 3 groups independently selected from:
  (a) hydroxy,
  (b) halogen,
  (c) —CO$_2$R$^3$,
  (d) —CONR$^3$R$^3$, and
  (e) —NR$^3$R$^3$;

Z is selected from the group consisting of:
(1) phenyl,
(2) 5 or 6-membered heterocyclic ring with from 1 to 4 heteroatoms independently selected from oxygen, sulfur and nitrogen,
(3) a C$_5$-C$_8$ carbocyclic ring fused to a 5 or 6-membered heterocyclic ring with from 1 to 4 heteroatoms independently selected from oxygen, sulfur and nitrogen, and
(4) 5 or 6-membered heterocyclic ring with from 1 to 4 heteroatoms independently selected from oxygen, sulfur and nitrogen fused to a 5 or 6-membered heterocyclic ring with from 1 to 4 heteroatoms independently selected from oxygen, sulfur and nitrogen;

each occurrence of R$^1$ is independently selected from the group consisting of:

(1) $C_1$-$C_4$ alkyl optionally substituted with 1 to 3 groups independently selected from:
  (a) hydroxy,
  (b) halogen, and
  (c) $C_3$-$C_8$ cycloalkyl;
(2) $C_3$-$C_8$ cycloalkyl,
(3) oxo, and
(4) halogen;
each occurrence of $R^2$ is independently selected from the group consisting of:
(1) hydroxy,
(2) halogen,
(3) oxo,
(4) —$CO_2R^3$,
(5) $C_3$-$C_8$ cycloalkyl,
(6) —$S(O)_p$—$C_1$-$C_4$ alkyl,
(7) $C_1$-$C_4$ alkyl optionally substituted with 1 to 3 groups independently selected from
  (a) hydroxy,
  (b) halogen,
  (c) —$CO_2R^3$,
  (d) —$S(O)_p$—$C_1$-$C_4$ alkyl,
  (e) $C_3$-$C_8$ cycloalkyl, and
  (f) Z optionally substituted with 1 to 4 groups independently selected from hydroxyl, halogen, oxo, trifluoromethyl, trifluoromethoxy, $C_1$-$C_4$ alkyl, $C_1$-$C_4$ alkoxy, and —$CO_2R^3$, and
(8) Z optionally substituted with 1 to 4 groups independently selected from hydroxyl, halogen, oxo, trifluoromethyl, trifluoromethoxy, $C_1$-$C_4$ alkyl, $C_1$-$C_4$ alkoxy, —$SO_2$—$CH_3$, and —$CO_2R^3$; and
each occurrence of $R^3$ is independently selected from the group consisting of:
(1) hydrogen, and
(2) $C_1$-$C_4$ alkyl optionally substituted with 1 to 2 groups independently selected from phenyl, halogen, cyano and hydroxyl.

In one embodiment of formula I, m is 0, 1 or 2. In another embodiment, m is 0.

In one embodiment of formula I, n is 0, 1, 2 or 3. In another embodiment, n is 0, 1 or 2.

In one embodiment of formula I, m is 0 and n is 0, 1, 2 or 3

In one embodiment of formula I, p is 0 or 1. In another embodiment, p is 1.

In one embodiment of formula I, U is —CH= or —N=. In another embodiment, U is —CH—. In yet another embodiment, U is —N=.

In one embodiment of formula I, V is selected from the group consisting of (1) —O—; (2) —N=; and (3) —$NR^2$—. In another embodiment, V is —N= or —NH—. In yet another embodiment, V is —NH—.

In one embodiment of formula I, W is —N= or —$NR^2$—. In another embodiment, W is —NH—.

In one embodiment of formula I, V is —NH— and W is —N=.

In one embodiment of formula I, X is selected from the group consisting of:
(1) a bond, and
(2) $C_1$-$C_4$ alkanediyl optionally substituted with 1 to 2 groups independently selected from hydroxy and halogen.

In another embodiment, X is selected from the group consisting of (1) a bond, (2) —$CH_2$—, (3) —$CH_2CH_2$—, (4) —$CH(CH_3)$—, (5) —$CH_2CH_2CH_2$—, and (6) —$CH_2(CH_3)CH_2$—.

In one embodiment of formula I, Z is selected from the group consisting of:

(1) phenyl,
(2) a 5-membered heterocyclic ring having 1 N ring atom and 0 to 2 additional hetero ring atoms independently selected from N, O and S,
(3) a 6-membered heterocyclic ring having 1 N ring atom and 0 to 2 additional hetero ring atoms independently selected from N, O and S,
(4) a $C_5$-$C_6$ carbocyclic ring fused to a 5-membered heterocyclic ring having 1 N ring atom and 0 to 2 additional hetero ring atoms independently selected from N, O and S,
(5) a $C_5$-$C_6$ carbocyclic ring fused to a 6-membered heterocyclic ring having 1 N ring atom and 0 to 2 additional hetero ring atoms independently selected from N, O and S,
(6) a 5-membered heterocyclic ring having 1 N ring atom and 0 to 2 additional hetero ring atoms independently selected from N, O and S fused to a 5-membered heterocyclic ring having 1 N ring atom and 0 to 2 additional hetero ring atoms independently selected from N, O and S,
(7) a 5-membered heterocyclic ring having 1 N ring atom and 0 to 2 additional hetero ring atoms independently selected from N, O and S fused to a 6-membered heterocyclic ring having 1 N ring atom and 0 to 2 additional hetero ring atoms independently selected from N, O and S, and
(8) a 6-membered heterocyclic ring having 1 N ring atom and 0 to 2 additional hetero ring atoms independently selected from N, O and S fused to a 6-membered heterocyclic ring having 1 N ring atom and 0 to 2 additional hetero ring atoms independently selected from N, O and S.

In another embodiment, Z is selected from the group consisting of:
(1) phenyl,
(2) a 5-membered heterocyclic ring having 1 N ring atom and 0 to 2 additional hetero ring atoms independently selected from N, O and S,
(3) a 6-membered heterocyclic ring having 1 N ring atom and 0 to 2 additional hetero ring atoms independently selected from N, O and S,
(4) a $C_5$-$C_6$ carbocyclic ring fused to a 5-membered heterocyclic ring having 1 N ring atom and 0 to 2 additional hetero ring atoms independently selected from N, O and S,
(5) a 5-membered heterocyclic ring having 1 N ring atom and 0 to 2 additional hetero ring atoms independently selected from N, O and S fused to a 5-membered heterocyclic ring having 1 N ring atom and 0 to 2 additional hetero ring atoms independently selected from N, O and S, and
(6) a 5-membered heterocyclic ring having 1 N ring atom and 0 to 2 additional hetero ring atoms independently selected from N, O and S fused to a 6-membered heterocyclic ring having 1 N ring atom and 0 to 2 additional hetero ring atoms independently selected from N, O and S.

In yet another embodiment, Z is selected from the group consisting of phenyl, thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,2,5-oxadiazolyl,

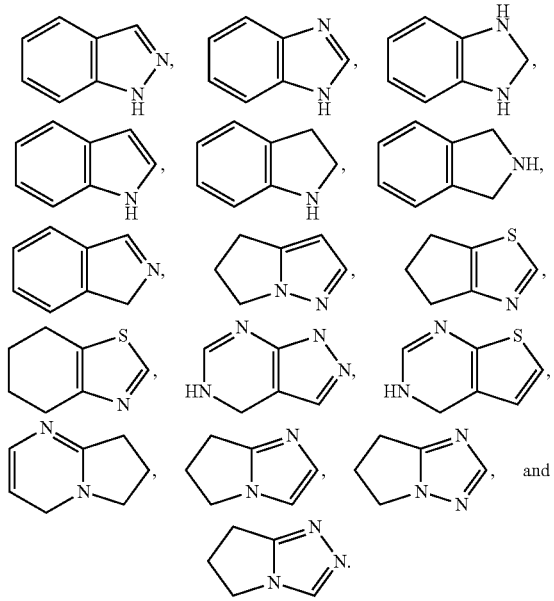

In still another embodiment, Z is selected from the group consisting of phenyl, thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,2,5-oxadiazolyl,

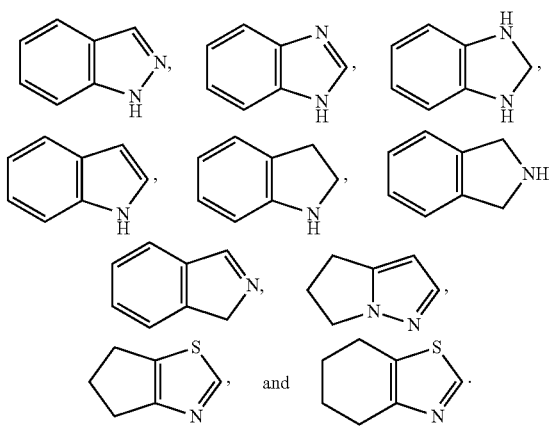

In one embodiment of formula I, each occurrence of $R^2$ is independently selected from the group consisting of:
(1) hydroxy,
(2) halogen,
(3) oxo,
(4) —$CO_2H$,
(5) methyl, ethyl or propyl, each of which optionally substituted with 1 to 2 groups independently selected from hydroxyl and halogen,
(6) —$SO_2$—$CH_3$, and
(7) Z optionally substituted with 1 to 4 groups independently selected from hydroxyl, halogen, oxo, trifluoromethyl, trifluoromethoxy, $C_1$-$C_4$ alkyl, $C_1$-$C_4$ alkoxy, and —$CO_2H$.

In one embodiment of formula I, each occurrence of $R^3$ is independently selected from the group consisting of:

(1) hydrogen,
(2) methyl, and
(3) ethyl.

In one embodiment, compounds disclosed herein have formula (Ia):

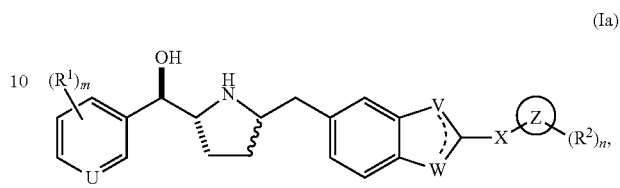

(Ia)

or a pharmaceutically acceptable salt thereof, wherein m, n, p, U, V, W, X, Z, $R^1$ and $R^2$ are as defined above under formula (I).

In another embodiment, compounds disclosed herein have formula (Ib):

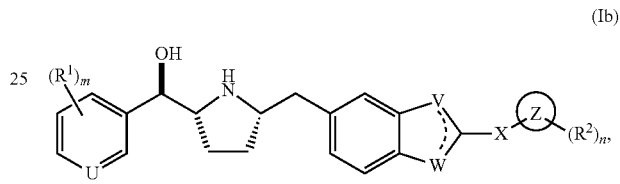

(Ib)

or a pharmaceutically acceptable salt thereof, wherein m, n, p, U, X, Z, $R^1$ and $R^2$ are as defined above under formula (I).

In another embodiment, compounds disclosed herein have formula (Ic):

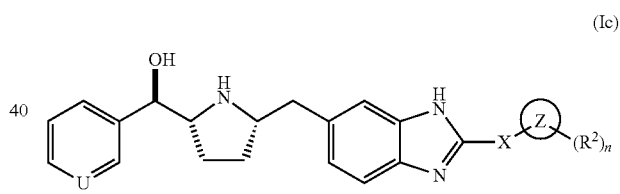

(Ic)

or a pharmaceutically acceptable salt thereof, wherein n, U, X, Z and $R^2$ are as defined above under formula (I).

In one embodiment of formula Ic,
n is 0, 1, 2, 3 or 4;
U is —CH= or —N=;
X is selected from the group consisting of:
(1) a bond,
(2) —$CH_2$—,
(3) —$CH_2(CH_3)$—
(4) —$CH_2CH_2$—,
(5) —$CH_2(CH_3)CH_2$—, and
(6) —$CH_2CH_2CH_2$—;
Z is selected from the group consisting of:
(1) phenyl,
(2) a 5-membered heterocyclic ring having 1 N ring atom and 0 to 2 additional hetero ring atoms independently selected from N, O and S,
(3) a 6-membered heterocyclic ring having 1 N ring atom and 0 to 2 additional hetero ring atoms independently selected from N, O and S,
(4) a $C_5$-$C_6$ carbocyclic ring fused to a 5-membered heterocyclic ring having 1 N ring atom and 0 to 2 additional hetero ring atoms independently selected from N, O and S, (5) a 5-membered heterocyclic ring having 1 N ring atom and 0 to 2 additional hetero ring atoms independently selected from N, O and S fused to a 5-membered heterocyclic ring having 1 N ring atom and 0 to 2 additional hetero ring atoms independently selected from N, O and S, and
(6) a 5-membered heterocyclic ring having 1 N ring atom and 0 to 2 additional hetero ring atoms independently selected from N, O and S fused to a 6-membered heterocyclic ring having 1 N ring atom and 0 to 2 additional hetero ring atoms independently selected from N, O and S;

each occurrence of $R^2$ is independently selected from the group consisting of:
(1) hydroxy,
(2) halogen,
(3) oxo,
(4) —$CO_2R^3$,
(5) —$SO_2R^3$,
(6) $C_1$-$C_4$ alkyl optionally substituted with 1 to 3 groups independently selected from
    (a) hydroxy,
    (b) halogen,
    (c) —$CO_2R^3$,
    (d) —$SO_2R^3$, and
    (e) Z optionally substituted with 1 to 4 groups independently selected from hydroxyl, halogen, oxo, trifluoromethyl, trifluoromethoxy, $C_1$-$C_4$ alkyl, $C_1$-$C_4$ alkoxy, and —$CO_2R^3$, and
(7) Z optionally substituted with 1 to 4 groups independently selected from hydroxyl, halogen, oxo, trifluoromethyl, trifluoromethoxy, $C_1$-$C_4$ alkyl, $C_1$-$C_4$ alkoxy, —$SO_2R^3$, and —$CO_2R^3$; and each occurrence of $R^3$ is independently selected from the group consisting of:
(1) hydrogen, and
(2) $C_1$-$C_4$ alkyl.

In another embodiment of formula Ic, Z is selected from the group consisting of: phenyl, thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,2,5-oxadiazolyl,

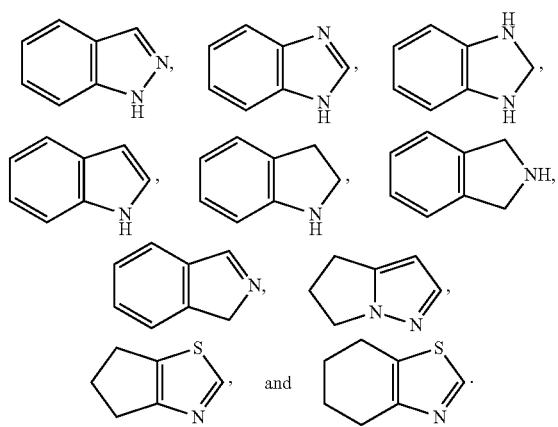

In yet another embodiment of formula Ic, each occurrence of $R^2$ is independently selected from the group consisting of:

(1) hydroxy,
(2) halogen,
(3) oxo,
(4) —$CO_2H$,
(5) —$CO_2CH_3$,
(6) methyl, ethyl or propyl, each of which optionally substituted with 1 to 2 groups independently selected from hydroxy, halogen and Z optionally substituted with 1 to 4 groups independently selected from hydroxyl, halogen, oxo, trifluoromethyl, trifluoromethoxy, methyl, ethyl, —$CO_2H$, and —$CO_2CH_3$,
(7) —$SO_2$—$CH_3$, and
(8) Z optionally substituted with 1 to 4 groups independently selected from hydroxyl, halogen, oxo, trifluoromethyl, trifluoromethoxy, methyl, ethyl and —$CO_2H$.

In still another embodiment of formula Ic, each occurrence of $R^2$ is independently selected from the group consisting of:
(1) hydroxy,
(2) fluoro,
(3) oxo,
(4) —$CO_2H$,
(5) methyl or ethyl, each of which optionally substituted with 1 to 2 groups independently selected from hydroxy, halogen and Z optionally substituted with 1 to 3 groups independently selected from hydroxyl, halogen, oxo, trifluoromethyl, methyl, ethyl, and —$CO_2H$,
(6) —$SO_2$—$CH_3$, and
(7) Z optionally substituted with 1 to 3 groups independently selected from hydroxyl, halogen, oxo, trifluoromethyl, methyl, ethyl, and —$CO_2H$.

As used herein, the term "alkyl" means both branched- and straight-chain saturated aliphatic hydrocarbon groups having the specified number of carbon atoms. For example, $C_1$-$C_6$ alkyl includes, but is not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tert-butyl (t-Bu), isopentyl, sec-pentyl, tert-pentyl, isohexyl and the like.

The term "cycloalkyl" means a monocyclic saturated carbocyclic ring, having the specified number of carbon atoms, e.g., 3, 4, 5 or 6 carbon atoms. Non-limiting examples of $C_3$-$C_6$ cycloalkyl include cyclopropyl, cyclobutyl, cyclopentyl and cyclohexyl.

The term "alkanediyl" means a straight or branched divalent hydrocarbon radical having the specified number of carbon atoms. Non-limiting examples of $C_1$-$C_4$ "alkanediyl" include, but are not limited to, methylene (—$CH_2$—), ethylene (—$CH_2CH_2$—), 1,1-ethanediyl (—$CH(CH_3)$—), 1,2-propanediyl (—$CH(CH_3)CH_2$—), 2-methyl-1,1-propanediyl (—$CH[C(CH_3)_2]$), 1,4-butanediyl (—$CH_2CH_2CH_2CH_2$—), 2,3-butanediyl (—$CH(CH_3)CH(CH_3)$—, and the like. One example of a halogen substituted alkanediyl is —$C(CH_3)(F)$—.

The term "optionally substituted" means "unsubstituted or substituted," and therefore, the generic structural Formulas described herein encompass compounds containing the specified optional substituent as well as compounds that do not contain the optional substituent. Each variable is independently defined each time it occurs within the generic structural formula definitions.

The terms "halo" or "halogen" are meant to include fluoro, chloro, bromo and iodo, unless otherwise noted.

The terms "carbocycle" or "carbocyclic" refer to saturated, partially unsaturated and aromatic rings having only ring carbon atoms. For example, $C_5$-$C_{10}$ carbocyclic ring include, but are not limited to, cyclopentyl, cyclohexyl, cycloheptyl, cyclooctyl, cyclopentenyl, cyclohexenyl, cyclohexadienyl, and phenyl.

The term "aryl" refers to an aromatic carbocycle.

The terms "heterocycle" or "heterocyclic" refer to saturated, partially unsaturated and aromatic rings having at least one, ring heteroatom and at least one ring carbon atom; the heterocycle may be attached to the rest of the molecule via a ring carbon atom or a ring hetero atom, for example, a ring nitrogen atom. The terms "heteroaryl" or "heteroaromatic" refer to an aromatic heterocycle. For example, within the definition for Z, the term "a 5- or 6-membered heterocyclic ring with from 1 to 4 heteroatoms selected from oxygen, sulfur and nitrogen" includes, but is not limited to, pyrrolyl, thienyl, furanyl, imidazolyl, pyrazolyl, oxazolyl, isoxazolyl, thiazolyl, isothiazolyl, triazolyl, tetrazolyl, oxadiazolyl, thiadiazolyl, pyrrolidinyl, tetrahydrofuranyl, pyridinyl, dihydropyridinyl, tetrahydropyridinyl, pyrimidinyl, dihydropyrimidinyl, tetrahydropyrimidinyl, pyrazinyl, dihydropyrazinyl, tetrahydropyrazinyl, pyridazinyl, dihydropyridazinyl, tetrahydropyridazinyl, piperidinyl, piperazinyl, morpholinyl, pyranyl, dihydropyranyl, tetrahydropyranyl, and the like.

Within the definition for Z, the term "a benzene ring fused to a $C_5$-$C_{10}$ carbocyclic ring" includes, but is not limited to, naphthyl, dihydronaphthyl, tetrahydronaphthyl, indanyl, indenyl, benzocycloheptene, tetrahydrobenzocyloheptene, and the like. In one embodiment, a benzene ring is fused to a $C_5$-$C_6$ carbocyclic ring. Such fused ring may be attached to the rest of the molecule via a carbon atom on either ring.

Within the definition for Z, the term "a 5- or 6-membered heterocyclic ring with from 1 to 4 heteroatoms independently selected from oxygen, sulfur and nitrogen fused to a 5- or 6-membered heterocyclic ring with from 1 to 4 heteroatoms independently selected from oxygen, sulfur and nitrogen" includes, but is not limited to, naphthyridinyl, dihydronaphthyridinyl, tetrahydronaphthyridinyl, imidazopyridinyl, pteridinyl, purinyl, quinolizinyl, indolizinyl, tetrahydroquinolizinyl, and tetrahydroindolizinyl. In one embodiment, Z is selected from the group consisting of:

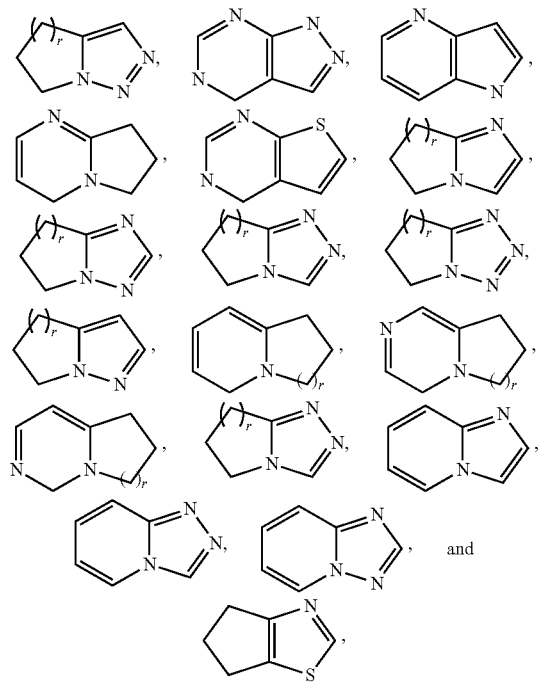

and wherein r is 1 or 2. Such fused ring may be attached to the rest of the molecule via a carbon atom or a nitrogen atom on either ring.

To avoid any doubt, the term "a 5- or 6-membered heterocyclic ring with from 1 to 4 heteroatoms independently selected from oxygen, sulfur and nitrogen fused to a 5- or 6-membered heterocyclic ring with from 1 to 4 heteroatoms independently selected from oxygen, sulfur and nitrogen" as used herein includes compounds having only one nitrogen as the sole heteroatom when the nitrogen is located at the bridgehead.

Within the definition for Z, the term "a $C_5$-$C_{10}$ carbocyclic ring fused to a 5- or 6-membered heterocyclic ring with from 1 to 4 heteroatoms independently selected from oxygen, sulfur and nitrogen" includes, but is not limited to, indolyl, isoindolyl, benzofuranyl, benzothienyl, benzimidazolyl, benzotriazolyl, benzoxazolyl, benzisoxazolyl, benzthiazolyl, benzisothiazolyl, quinolinyl, isoquinolinyl, quinoxalinyl, quinazolinyl, cinnolinyl, indazolyl, tetrahydroquinolinyl, tetrahydroindazolyl, dihydroindazolyl, chromanyl, chromanyl benztriazolyl,

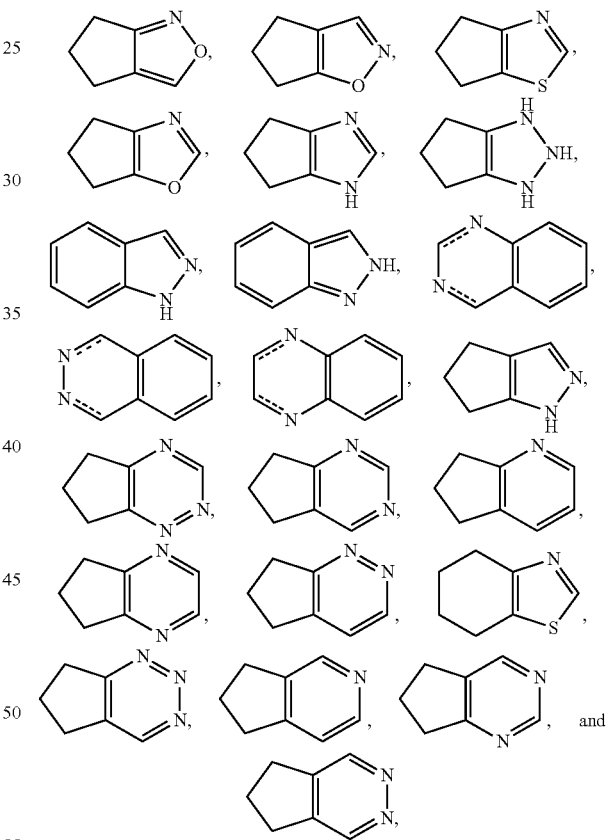

and where the dash bond "----" means a single or double bond while conforming to the valency rule for the ring atoms. Such fused ring may be attached to the rest of the molecule via a carbon atom on either ring or a nitrogen atom on the heterocyclic ring.

For the terms $(R^1)_m$ and $(R^2)_n$, as well as other similar notations, when m or n is 0, then $R^1$ or $R^2$ is hydrogen; when m or n is greater than 1, then each occurrence of $R^1$ or $R^2$ is independently selected from other occurrences of $R^1$ or $R^2$, respectively. For example, when n is 2, the two $R^2$ substituents can be the same or different.

In one embodiment, Z is a 5- or 6-membered heterocyclic ring with from 1 to 4 heteroatoms independently selected from oxygen, sulfur and nitrogen. In one subset Z is a 5-membered heterocycle having one nitrogen atom and 0 to 2 additional heteroatoms independently selected from N, O and S. In another subset Z is a 6-membered heterocycle having 1, 2 or 3 nitrogen atoms, or 1 nitrogen atom and an oxygen or sulfur atom. In yet another subset, Z is selected from the group consisting of thiazolyl, oxazolyl, pyridyl, dihydropyridyl, triazolyl (including 1,2,4-triazolyl and 1,2,3-triazolyl), tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, and oxadiazolyl (including 1,2,4-oxadiazolyl and 1,2,5-oxadiazolyl).

In another embodiment, Z is a $C_5$-$C_8$ carbocyclic ring fused to a 5- or 6-membered heterocyclic ring with from 1 to 4 heteroatoms independently selected from oxygen, sulfur and nitrogen. In one subset the carbocyclic ring is a $C_5$-$C_6$ carbocyclic ring. In another subset the heterocycle is either a 5-membered heterocycle having one nitrogen atom and 0 to 3 additional heteroatoms independently selected from N, O and S, or a 6-membered heterocycle having 1, 2 or 3 nitrogen atoms, or 1 nitrogen atom and an oxygen or sulfur atom, and the carbocycle has 5 or 6 carbon atoms. In yet another subset Z is selected from the group consisting of: indolyl, benzimidazolyl, benzthiazolyl, quinolinyl, isoquinolinyl, tetrahydroquinolinyl, tetrahydroisoquinolinyl, chromenyl, benztriazolyl,

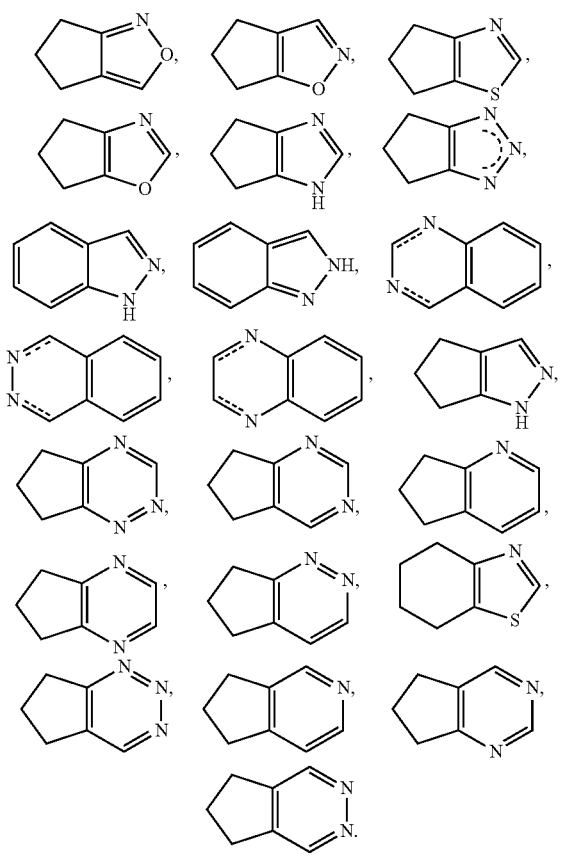

In another embodiment, Z is a 5- or 6-membered heterocyclic ring with from 1 to 4 heteroatoms independently selected from oxygen, sulfur and nitrogen fused to a 5- or 6-membered heterocyclic ring with from 1 to 4 heteroatoms independently selected from oxygen, sulfur and nitrogen. In one subset the fused ring has 2 to 5 heteroatoms, at least one of which is nitrogen. In another subset the fused ring has 2 to 4 nitrogen atoms and no other heteroatoms. In yet another subset the fused ring has one oxygen or sulfur atom, and 1 to 3 nitrogen atoms. In yet another subset, Z is selected from the group consisting of

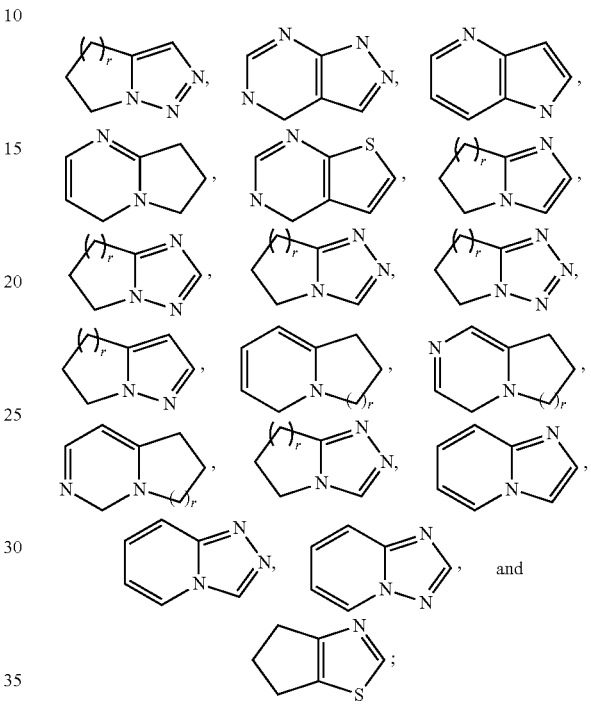

and wherein r is 1 or 2.

In one embodiment, compounds described herein are as described in the Examples below.

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. The above Formulas I and Ia are shown without a definitive stereochemistry at certain positions. The present invention includes all stereoisomers of Formulas I and Ia and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound described herein may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —$CH=C(OH)$— groups (enol forms). Both keto and enol forms, individually as well as mixtures thereof, are included within the scope of the present invention.

Isotopes

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds described herein can be prepared without undue experimentation by conventional techniques well known to those skilled in the art or by processes analogous to those described in the Schemes and Examples herein using appropriate isotopically-enriched reagents and/or intermediates.

Salts

The term "pharmaceutically acceptable salt(s)" refers to salts prepared from pharmaceutically acceptable non-toxic bases or acids. When a compound described herein is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When a compound described herein is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds described herein. As used herein, the term "solvate" refers to a complex of variable stoichiometry formed by a solute (e.g., a compound of Formula I or Ia) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrates include, but are not limited to, hemi-, mono, sesqui-, di- and trihydrates.

Prodrugs

The present invention includes within its scope the prodrugs of the compounds described herein. In general, such prodrugs will be functional derivatives of the compounds described herein which are readily convertible in vivo into the required compound. Thus, in the methods of treatment of the present invention, the term "administering" shall encompass the treatment of the various conditions described with a compound described herein or with a compound which may not be a compound described herein, but which converts to a compound described herein in vivo after administration to the patient. Conventional procedures for the selection and preparation of suitable prodrug derivatives are described, for example, in "Design of Prodrugs," ed. H. Bundgaard, Elsevier, 1985.

Utilities

Compounds described herein are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeutically effective amount of a compound described herein. The term "mammal" includes human and non-human animals such as dogs and cats and the like. The diseases, disorders or conditions for which compounds of the present invention are useful in treating or preventing include, but are not limited to, (1) overactive bladder, (2) urinary incontinence, (3) urge urinary incontinence, (4) urinary urgency, (5) diabetes mellitus, (6) hyperglycemia, (7) obesity, (8) hyperlipidemia, (9) hypertriglyceridemia, (10) hypercholesterolemia, (11) atherosclerosis of coronary, cerebrovascular and peripheral arteries, (12) gastrointestinal disorders including peptide ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (13) neurogenic inflammation of airways, including cough, asthma, (14) depression, (15) prostate diseases such as benign prostate hyperplasia, (16) irritable bowel syndrome and other disorders needing decreased gut motility, (17) diabetic retinopathy, (18) preterm labor, and (19)-elevated intraocular pressure and glaucoma.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds described herein are administered orally.

The effective dosage of active ingredient employed may vary depending on the particular compound employed, the mode of administration, the condition being treated and the severity of the condition being treated. Such dosage may be ascertained readily by a person skilled in the art.

When treating overactive bladder (OAB) in conjunction with other anti-OAB agents, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release form. In the case of a 70 kg adult human, the total daily dose will generally be from about 0.7 mg to about 3500 mg, or more specifically, from about 0.7 mg to about 2000 mg. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release form. In the case of a 70 kg adult human, the total daily dose will generally be from about 0.7 mg to about 3500 mg. This dosage regimen may be adjusted to provide the optimal therapeutic response.

When treating diabetes mellitus and/or hyperglycemia, as well as other diseases or disorders for which compounds described herein are useful, generally satisfactory results are obtained when the compounds of the present invention are administered at a daily dosage of from about 0.001 mg to about 100 mg per kg of animal body weight, preferably given in a single dose or in divided doses two to six times a day, or in sustained release form. In the case of a 70 kg adult human, the total daily dose will generally be from about 0.07 mg to about 350 mg. This dosage regimen may be adjusted to provide the optimal therapeutic response.

In one embodiment, a compound of the present invention is used in the manufacture of a medicament for the treatment or prevention of a disease or disorder mediated by the activation of $\beta 3$-adrenoceptor.

Another aspect of the present invention provides pharmaceutical compositions which comprises a compound described herein and a pharmaceutically acceptable carrier. The pharmaceutical compositions of the present invention comprise a compound described herein as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, intravesical, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds described herein can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds described herein may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Compounds described herein may be used in combination with other drugs that are used in the treatment/prevention/suppression or amelioration of the diseases or conditions for which compounds described herein are useful. Such other drugs may be administered, by a route and in an amount commonly used therefor, contemporaneously or sequentially with a compound described herein. When a compound described herein is used contemporaneously with one or more other drugs, a pharmaceutical unit dosage form containing such other drugs in addition to the compound described herein is preferred. Accordingly, the pharmaceutical compositions of the present invention include those that also contain one or more other active ingredients, in addition to a compound described herein. Examples of other active ingredients that may be combined with a compound described herein, either administered separately or in the same pharmaceutical compositions, include, but are not limited to:

(a) overactive bladder medicines including (i) muscarinic receptor antagonists (e.g. tolterodine, oxybutynin including S-oxybutynin, hyoscyamine, propantheline, propiverine, trospium including trospium chloride, solifenacin, darifenacin, imidafenacin, fesoterodine, temiverine, SVT-40776, 202405 by GlaxoSmithKline, TD6301, RBX9841, DDP200, PLD179, and other anticholinergics. See, for example, U.S. Pat. No. 5,382,600; U.S. Pat. No. 3,176,019; U.S. Pat. No. 3,480,626; U.S. Pat. No. 4,564,621; U.S. Pat. No. 5,096,890; U.S. Pat. No. 6,017,927; U.S. Pat. No. 6,174,896; U.S. Pat. No. 5,036,098; U.S. Pat. No. 5,932,607; U.S. Pat. No. 6,713,464; U.S. Pat. No. 6,858,650; and DD 106643. See also, U.S. Pat. No. 6,103,747; U.S. Pat. No. 6,630,162; U.S. Pat. No. 6,770,295; U.S. Pat. No. 6,911,217; U.S. Pat. No. 5,164,190; U.S. Pat. No. 5,601,839; U.S. Pat. No. 5,834,010; U.S. Pat. No. 6,743,441; WO2002000652; WO200400414853. As will be appreciated by those of skill in the art, these drugs may be administered orally or topically in standard or extended release forms, such as extended release tolterodine, extended release oxybutynin and transdermal oxybutynin), (ii) NK-1 or NK-2 antagonists (e.g. aprepitant, cizolirtine, compounds described in WO2005/073191, WO2005/032464, and other reported NK-1 antagonists), (iii) alpha adrenergic receptor antagonists (e.g. alfuzosin, doxazosin, prazosin, tamsulosin, terazosin, and others), (iv) potassium channel openers (e.g. cromakalim, pinacidil, and others), (v) vanilloids and other afferent-nerve modulators—agonists and antagonists (e.g. capsaicin, resiniferatoxin, and others), (vi) dopamine D1 receptor agonists (e.g. pergolinde), (vii) serotonergic and/or norepinephrine reuptake inhibitors (e.g. duloxetine), (viii) neuromuscular junction inhibition of acetylcholine release (e.g. botulinum toxin), (ix) calcium channel blockers (e.g. diltiazem, nifedipine, verapamil, and others), (x) inhibitors of prostaglandin synthesis (e.g. flurbiprofen), (xi) gamma aminobutyric acid receptor antagonists (e.g. baclofen), (xii) vaginal estrogen preparations (xiii) selective norepinephrine reuptake inhibitors, (xiv) 5-HT2C agonists, (xv) voltage gated sodium channel blocker, (xvi) P2X purinergic receptor antagonists (e.g. P2X1 or P2X3 antagonists), (xvii) PAR2 inhibitors, (xviii) phosphodiesterase inhibitors (e.g. PDE1, PDE4, and PDE5 inhibitors); and (xix) ATP sensitive potassium channel openers.

(b) insulin sensitizers including (i) PPARγ agonists such as the glitazones (e.g. troglitazone, pioglitazone, englitazone, MCC-555, BRL49653 and the like), and compounds described in WO97/27857, 97/28115, 97/28137 and 97/27847; (ii) biguanides such as metformin and phenformin;

(c) insulin or insulin mimetics;

(d) sulfonylureas such as tolbutamide and glipizide;

(e) α-glucosidase inhibitors (such as acarbose), (f) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activator receptor α agonists such as fenofibric acid derivatives (gemfibrozil, clofibrat, fenofibrate and benzafibrate), (iv) inhibitors of cholesterol absorption for example beta-sitosterol and ezetimibe, and (acyl CoA:cholesterol acyltransferase) inhibitors for example melinamide, (v) probucol, (vi) vitamin E, and (vii) thyromimetics;

(g) PPARδ agonists such as those disclosed in WO97/28149;

(h) antiobesity compounds such as fenfluramine, dexfenfluramine, phentermine, sibutramine, orlistat, and other $\beta_3$ adrenergic receptor agonists;

(i) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(j) PPARα agonists such as described in WO 97/36579 by Glaxo;

(k) PPARγ antagonists as described in WO97/10813; and (l) serotonin reuptake inhibitors such as fluoxetine and sertraline.

In one embodiment, a compound of the present invention and a second active agent as described above are used in the manufacture of a medicament for the treatment or prevention of a disease or disorder mediated by the activation of β3-adrenoceptor.

The compounds of disclosed herein can be prepared according to the procedures of the following Schemes and Examples using appropriate materials, and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

A variety of chromatographic techniques may be employed in the preparation of the compounds. These techniques include, but are not limited to: High Performance Liquid Chromatography (HPLC) including normal phase, reversed phase, and chiral phase HPLC; Medium Pressure Liquid Chromatography (MPLC), Super Critical Fluid Chromatography; preparative Thin Layer Chromatography (prep TLC); flash chromatography with silica gel or reversed-phase silica gel; ion-exchange chromatography; and radial chromatography. All temperatures are degrees Celsius unless otherwise noted.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Throughout the application, the following terms have the indicated meanings unless noted otherwise:

| Term | Meaning |
| --- | --- |
| Ac | Acyl (CH₃C(O)—) |
| Aq. | Aqueous |
| Bn | Benzyl |
| BOC (Boc) | t-Butyloxycarbonyl |
| BOP | Benzotriazol-1-yloxytris(dimethylamino)phosphonium hexafluorophosphate |
| ° C. | Degree Celsius |
| Calc. or calc'd | Calculated |
| Celite | Celite ™ diatomaceous earth |
| DCC | Dicyclohexylcarbodiimide |
| DCM | Dichloromethane |
| DIEA | N,N-diisopropyl-ethylamine |
| DMAP | 4-Dimethylaminopyridine |
| DMF | N,N-dimethylformamide |
| EDC | 1-Ethyl-3-(3-dimethylaminopropyl) carbodiimide |
| Eq. or equiv. | Equivalent(s) |
| ES-MS and ESI-MS | Electron spray ion-mass spectroscopy |
| Et | Ethyl |
| EtOAc | Ethyl acetate |
| g | Gram(s) |
| h or hr | Hour(s) |
| HATU | O-(7-azabenzotriazol-1-yl)-N, N, N', N'-tetramethyluronium hexafluorophosphate |
| HCl | Hydrogen chloride |
| HOAc | Acetic acid |
| HOAT | 1-Hydroxy-7-azabenzotriazole |
| HOBT | 1-Hydroxybenzotriazole |
| HPLC | High performance liquid chromatography |
| IPA | Isopropyl alcohol |
| kg | Kilogram(s) |
| LC/MS or LC-MASS | Liquid chromatography mass spectrum |
| L | Liter(s) |
| LDA | Lithium diisopropylamide |
| LiOH | Lithium hydroxide |
| LiHMDS | Lithium bis(trimethylsilyl)amide |
| M | Molar(s) |
| Me | Methyl |
| MeOH | Methanol |
| MF | Molecular formula |
| min | Minute(s) |
| mg | Milligram(s) |
| mL | Milliliter(s) |
| mmol | Millimole(s) |
| MOZ (Moz) | p-Methoxybenzyloxycarbonyl |

-continued

| Term | Meaning |
| --- | --- |
| MP | Melting point |
| MS | Mass spectrum |
| NaH | Sodium hydride |
| nM | Nanomolar |
| OTf | Trifluoromethanesulfonyl |
| 10% Pd/C | Palladium, 10 weight percent on activated carbon |
| Ph | Phenyl |
| Prep. | Preparative |
| Ref. | Reference |
| r.t. or rt or RT | RT |
| Sat. | Saturated |
| SCF CO₂S | Super critical fluid carbon dioxide |
| TBAF | Tetrabutylammonium fluoride |
| TBAI | Tetrabutylammonium iodide |
| TBDPS | Tert-butyl diphenylsilyl |
| TBS, TBDMS | Tert-butyl dimethylsilyl |
| TEA or Et₃N | Triethylamine |
| Tf | Triflate or trifluoromethanesulfonate |
| TFA | Trifluoroacetic acid |
| THF | Tetrahydrofuran |
| TLC | Thin-layer chromatography |
| TMS | Trimethylsilyl |
| TMSOK | Potassium trimethylsilanolate |

Reaction Schemes below illustrate the methods employed in the synthesis of the compounds described herein. All substituents are as defined above unless indicated otherwise. The synthesis of the novel compounds described herein may be accomplished by one or more of several similar routes. The Examples further illustrate details for the preparation of the compounds described herein. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless noted otherwise. Mass spectra (MS) were measured by electron-spray ion-mass spectroscopy.

Scheme I

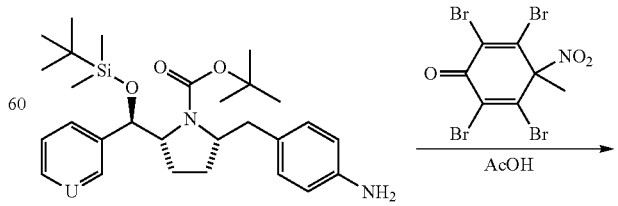

(U = N, CH)

I-1

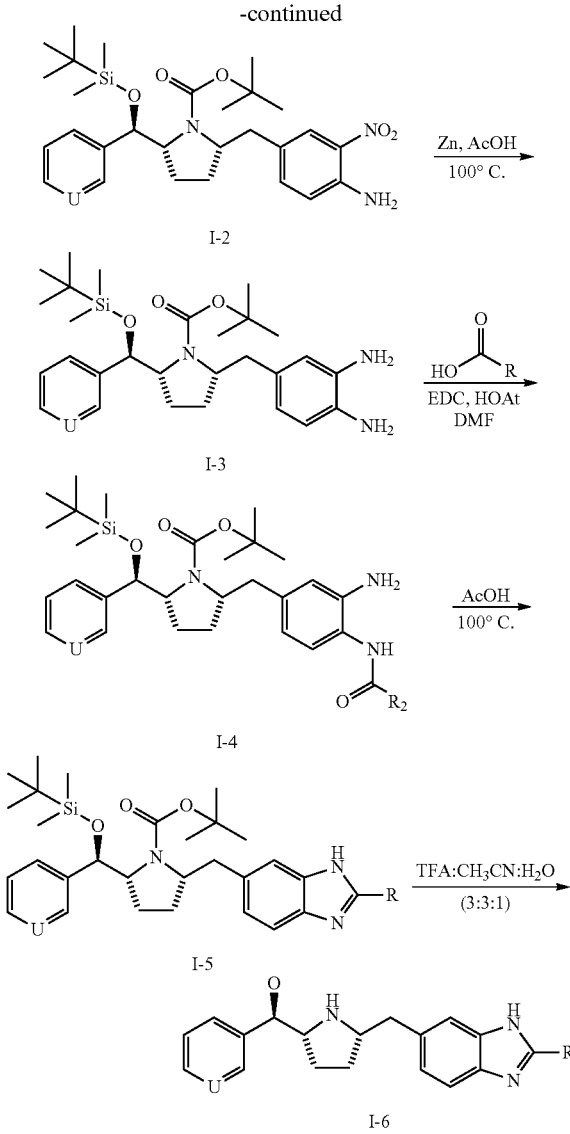

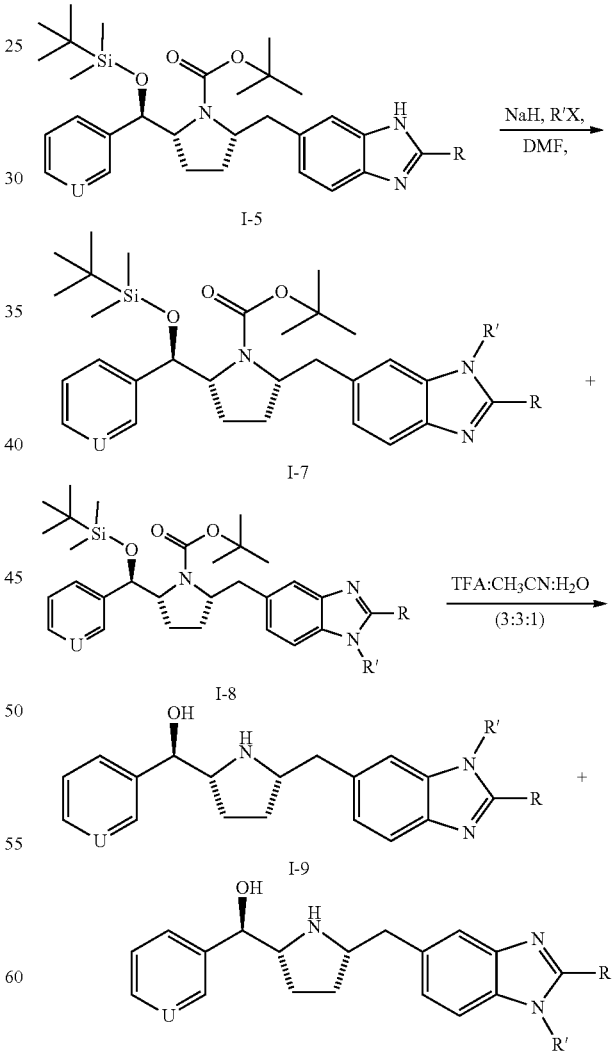

was achieved by heating a solution of I-4 in acetic acid to 100° C. for a period of between 2-24 h. Removal of the Boc and silyl protecting groups of I-5 simultaneously via treatment with a 3:3:1 mixture of acetonitrile:TFA:water at a temperature of 50° C. for a period of time between 1 and 6 h affords benzimidazoles of formula I-6.

Alternatively, sequential treatment of I-5 with a tetrabutylammonium fluoride solution in THF containing 5% water followed by treatment with a TFA solution in dichloromethane also yields the desired product of structural formula I-6. Additional deprotection steps may be included if there are useful protecting groups known to those skilled in the art on the R moiety necessary to allow the chemistry to proceed in a facile fashion. These protecting groups may include trityl groups, tert-butylcarbamate groups or other groups suitable for the protection of heterocyclic compounds or the functional groups attached to the R group, such as amines, hydroxyls, carboxylic acids or other groups known to those skilled in the art.

Scheme I describes the preparation of benzimidazole analogs of structural formula I-6 from the pyrrolidine intermediate I-1 by methods known to those skilled in the art. For example, treatment of I-1 with 2,3,5,6-tetrabromo-4-methyl-4-nitrocyclohexa-2,5-dien-1-one at 0° C. in the presence of acetic acid affords the nitrated product I-2. Reduction of the nitro group of I-2 is carried out in a heated solution of acetic acid in the presence of zinc metal to afford the bis-aniline I-3. Depending upon the choice of the carboxylic acid used, which are either commercially available, known in the literature or readily prepared by methods commonly known to those skilled in the art, I-3 can be converted to corresponding amide by using the appropriate method known to those skilled in the art. For example, compound I-3 and a desired carboxylic acid can be treated with N-(3-dimethylaminopropyl)-N'-ethylcarbodiimide hydrochloride and 1-hydroxy-7-azabenzotriazole (HOAt) in the presence of a suitable organic base, such as N,N-diisopropylethylamine. The reaction is usually performed in an inert organic solvent such as N,N-dimethylformamide, at room temperature for a period of 2-24 h, and the product is the amide of structural formula I-4. The preparation of benzimidazoles of general structural formula I-5

Scheme II describes the preparation of the alkylated benzimidazole analogs of structural formula I-9 and I-10 from intermediate I-5 by methods known to those skilled in the art. For example, treatment of I-5 with sodium hydride and the appropriate alkyl halide in a solvent such as N,N-dimethylformamide at 0-50° C. under an inert atmosphere for a period of 2-24 h affords products I-7 and I-8. Removal of the Boc and silyl protecting groups of I-7 and I-8 simultaneously via treatment with a 3:3:1 mixture of acetonitrile:TFA:water at a temperature of 50° C. for a period of time between 1 and 6 h affords benzimidazoles of formula I-9 and I-10. Alternatively, sequential treatment of I-7 and I-8 with a tetrabutylammonium fluoride solution in THF containing 5% water followed by treatment with a TFA solution in dichloromethane also yields the desired product of structural formula I-9 and I-10. Additional deprotection steps may be included if there are useful protecting groups known to those skilled in the art on the R moiety necessary to allow the chemistry to proceed in a facile fashion. These protecting groups may include trityl groups, tert-butylcarbamate groups or other groups suitable for the protection of heterocyclic compounds or the functional groups attached to the R group, such as amines, hydroxyls, carboxylic acids or other groups known to those skilled in the art.

In some cases the order of carrying out the foregoing reaction schemes may be varied to facilitate the reaction or to avoid unwanted reaction products. The following examples are provided so that the invention can be more fully understood. These examples are illustrative only and should not be construed as limiting the invention in any way.

Intermediate 1

Benzyl[3-(2-oxobut-3-en-1-yl)phenyl]carbamate
(i-1)

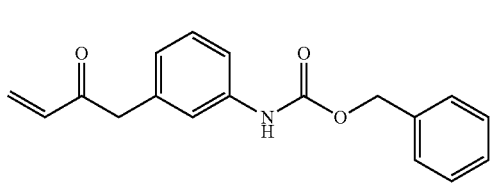

Step A: Ethyl(3-{[(benzyloxy)carbonyl]amino}phenyl)acetate

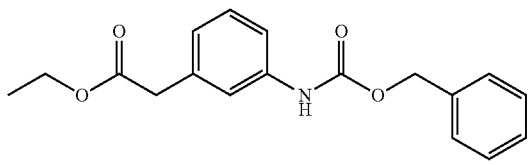 [SMILES: CCOC(=O)Cc1cccc(NC(=O)OCc2ccccc2)c1]

To a solution of methyl(3-aminophenyl)acetate (25 g, 140 mmol) in 250 mL anhydrous DCM was added DIEA (28.5 mL, 155 mmol) and the resulting solution cooled to 0° C. and set under nitrogen atmosphere. To this cooled solution was then added benzyl chloroformate (21.1 mL, 148 mmol) and the resulting mixture stirred overnight allowing to warm to room temperature. The reaction was washed with 1 M HCl, water, and then brine. The organic layer was dried over sodium sulfate, filtered and concentrated under vacuum. No further purification was necessary and the material (44 g, 99%) was used as is for the next step reaction. LC-MS: m/z (ES) 314 (MH)$^+$, 336 (MNa)$^+$.

Step B: (3-{[(Benzyloxy)carbonyl]amino}phenyl)acetic acid

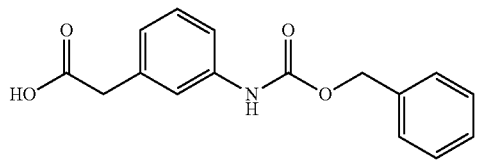 [SMILES: O=C(O)Cc1cccc(NC(=O)OCc2ccccc2)c1]

To a solution of 44.0 g (140 mmol) of ethyl(3-{[(benzyloxy)carbonyl]amino}phenyl)acetate) (from Step A) in THF, ethanol, and water (1:1:1, 1500 mL) was added solid LiOH (16.8 g, 700 mmol) and the resulting solution heated to 60° C. via oil bath for 3 h. The mixture was cooled to room temperature overnight and then 40 mL of concentrate HCl was slowly added, keeping the temperature below 25° C., until the solution was about pH of 2-3. Extract with ethyl acetate (3×750 mL) and then combine and wash organics with water and then brine. Dry organics over sodium sulfate, filter and concentrate under vacuum. The title compound (24.7 g, 87%) was used for the next step reaction without further purification. LC-MS: m/z (ES) 286 (MH)$^+$, 308 (MNa)$^+$.

Step C: Benzyl(3-{2-[methoxy(methyl)amino]-2-oxoethyl}phenyl)carbamate

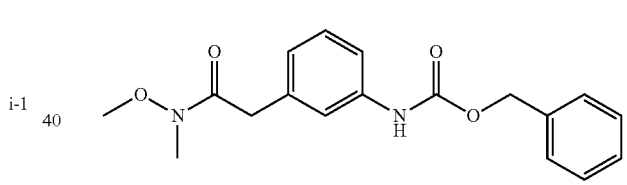

To a suspension of 24.7 g (87 mmol) of (3-{[(benzyloxy)carbonyl]amino}phenyl)acetic acid in 200 mL of dichloromethane (from Step B) was added triethylamine (30.2 mL, 173 mmol) which resulted in some exotherming (+5° C.) and the suspension becoming a solution. After 10 min cooling, HOBt (13.2 g, 87 mmol), N,O-dimethylhydroxylamine HCl (8.5 g, 87 mmol) was added to the solution followed by EDC (16.6 g, 87 mmol) and the resulting mixture stirred at room temperature overnight under nitrogen atmosphere. The solution was transferred to a separatory funnel and washed with 1 M HCl which caused an emulsion. Methanol was added to break up the emulsion and the aqueous was partitioned off. The organics were dried over sodium sulfate, filtered and concentrated under vacuum. Recrystallization of the residue from 1000 mL of 70% hexane in ethyl acetate (heated to reflux and then cooled to room temperature overnight) afforded the title compound (21 g, 74%) as a white solid. LC-MS: m/z (ES) 329 (MH)$^+$.

Step D: Benzyl[3-(2-oxobut-3-en-1-yl)phenyl]carbamate (i-1)

To a solution of 15 g (45.7 mmol) of benzyl(3-{2-[methoxy(methyl)amino]-2-oxoethyl}phenyl)carbamate (from Step C) in 1000 mL anhydrous THF under nitrogen atmosphere cooled to 0° C. via ice/water bath was added dropwise via cannula a 1.0 M solution of vinyl magnesium bromide (100 mL in THF, 100 mmol) and the resulting solution stirred for 1 h at 0° C. The reaction was quenched by a slow addition of 500 mL 1 M HCl keeping the temperature below 5° C. and stirred for 30 min. The mixture was then extracted with ethyl acetate and the combined organics washed with water followed by brine. The organics were then dried over sodium sulfate, filtered, and concentrate under vacuum. The residue was purified by Biotage 75M flash eluting with 30% ethyl acetate in hexane to afford the title compound (11 g, 78%) as a light yellow solid. LC-MS: m/z (ES) 310 (MH)+, 332 (MNa)+. $^1$HNMR (500 MHz, CDCl$_3$) δ: 7.44-7.36 (m, 7H), 7.18 (d, J=8.4 Hz, 2H), 6.70 (br s, 1H), 6.44 (dd, J=10.5, 17.6 Hz, 1H), 6.32 (dd, J=1.1, 17.6 Hz, 1H), 5.85 (dd, J=1.1, 10.5 Hz, 1H), 5.22 (s, 2H), 3.86 (s, 2H).

Intermediate 2

((1R)-1-[(R)-{[tert-butyl(dimethyl)silyl]oxy}(3-chlorophenyl)methyl]prop-2-en-1-yl}carbamate (i-2)

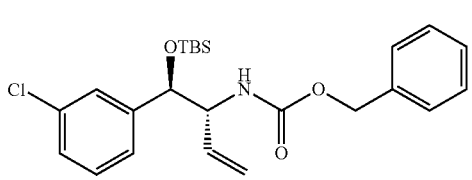

Step A: 1-(3-Chlorophenyl)prop-2-en-1-ol

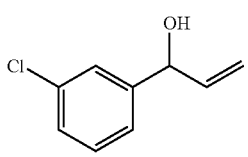

To a cooled solution of 3-chlorobenzaldehyde (22.5 g, 160 mmol) in 100 mL anhydrous THF under inert nitrogen atmosphere was added slowly via syringe a 1.6 M solution of vinyl magnesium chloride, in THF (100 mL, 160 mmol) and the solution stirred for three h allowing to warm to room temperature. The reaction was quenched with saturated solution of ammonium chloride and the organic layer was separated, extracted with ethyl acetate (2×200 mL), and organic layers were combined, dried over magnesium sulfate, filtered and concentrated under vacuum. Purification by Horizon MPLC with a 40M+ silica gel column using a gradient eluent of 0-40% ethyl acetate in hexane afforded the title compound (22.4 g, 44%). m/z (ES) 168, 170 (M, M+2)+, 190, 192 (MNa, MNa+2)+. $^1$HNMR (500 MHz, CDCl$_3$) δ: 7.38 (s, 1H), 7.35-722 (m, 3H), 5.90 (ddd, J=7.3, 10.0, 17.4 Hz, 1H), 5.38 (d, J=17.5 Hz, 1H), 5.18 (d, J=7.2 Hz, 1H), 5.15 (d, J=10.1 Hz, 1H), 0.96 (s, 9H), 0.18 (s, 3H), 0.08 (s, 3H).

Step B: Tert-butyl {[1-(3-chlorophenyl)prop-2-en-1-yl]oxy}dimethylsilane

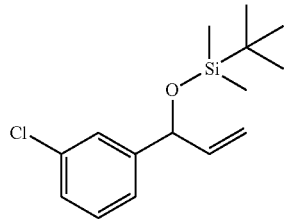 [SMILES: C=CC(O[Si](C)(C)C(C)(C)C)c1cccc(Cl)c1]

To a solution of 22.4 g (133 mmol) of 1-(3-chlorophenyl)prop-2-en-1-ol in 90 mL anhydrous DMF (from Step A) was added t-butyldimethylsilyl chloride (20.0 g, 133 mmol) and imidazole (18.1 g, 266 mmol) and the resulting solution was stirred overnight under nitrogen at room temperature. Wash with water and extract with ethyl acetate. Separate organics, dry over magnesium sulfate, filter, and concentrate under vacuum. The residue was purified by flash silica gel column eluting with a gradient eluent of 0-15% ethyl acetate in hexane to afford the title compound (16.6 g, 46%). m/z (ES) 282, 284 (M, M+2)+; 151, 153 (M-OTBS, M-OTBS+2)+.

Step C: {[Tert-butyl(dimethyl)silyl]oxy}(3-chlorophenyl)acetaldehyde

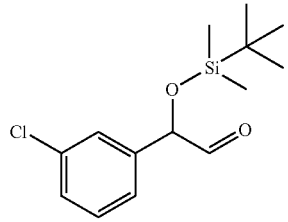 [SMILES: CC(C)(C)[Si](C)(C)OC(C=O)c1cccc(Cl)c1]

To a solution of 4.0 g (14.2 mmol) of tert-butyl {[1-(3-chlorophenyl)prop-2-en-1-yl]oxy}dimethylsilane in dichloromethane cooled to −78° C. via dry ice/acetone bath (from Step B) was bubbled ozone until the solution maintained a slight blue color. Nitrogen gas was then bubbled into the solution until it turned clear. Methyl sulfide was added to the solution and the resulting mixture was allowed to stir overnight at room temperature. The material was concentrated under vacuum and the residue purified via Horizon MPLC with a 40M+ silica gel column, eluting with a gradient eluent of 0-50% ethyl acetate in hexane to afford the product (3.57 g, 89%).

Step D: N-[(1E)-2-{[tert-butyl(dimethyl)silyl]oxy}-2-(3-chlorophenyl)ethylidene]-2-methylpropane-2-sulfinamide

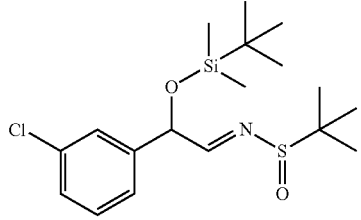 [SMILES: CC(C)(C)S(=O)/N=C/C(O[Si](C)(C)C(C)(C)C)c1cccc(Cl)c1]

To a solution of 3.0 g (10.6 mmol) of {[tert-butyl(dimethyl)silyl]oxy}(3-chlorophenyl)acetaldehyde (from Step C) and 1.3 g (10.6 mmol) of (R or S)-2-methyl-2-propanesulfinamide in 50 mL anhydrous dichloromethane was added copper (II) sulfate (3.4 g, 21.2 mmol) and the resulting mixture was stirred at room temperature under nitrogen atmosphere for 16 h. Wash reaction with water and extract with dichloromethane. Dry the organics with magnesium sulfate, filter and concentrate under vacuum. The residue was purified by Horizon MPLC, with a 40M+ silica gel column, eluting with a gradient eluent system of 0-25% ethyl acetate in hexane to afford the title compound (3.26 g, 80%). %). m/z (ES) 387, 390 (M, M+2)$^+$.

Step E: N-{1-[{[tert-butyl(dimethyl)silyl]oxy}(3-chlorophenyl)methyl]-prop-2-en-1-yl}2-methylpropane-2-sulfinamide

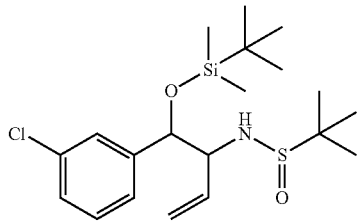 [SMILES: C=CC(NS(=O)C(C)(C)C)C(O[Si](C)(C)C(C)(C)C)c1cccc(Cl)c1]

To a solution of 2.4 g (6.20 mmol) of N-[(1E)-2-{[tert-butyl(dimethyl)silyl]oxy}-2-(3-chlorophenyl)ethylidene]-2-methylpropane-2-sulfinamide in 20 mL anhydrous THF cooled to 0° C. under nitrogen atmosphere (from Step D) was added a 1.6 M solution of vinyl magnesium chloride in THF (3.90 mL, 6.2 mmol) via syringe and the resulting mixture stirred for 1 h. The mixture was allowed to warm to room temperate and stirred for an additional hour. The reaction was quenched with saturated solution of ammonium chloride and extract with ethyl acetate. Combine organics, dry over magnesium sulfate, filter and concentrate under vacuum. The residue was purified by Horizon MPLC, with a 40M+ silica gel column, eluting with a gradient eluent system of 0-35% ethyl acetate in hexane to afford all four diastereomers as single isomers.

By NMR the four products obtained were diastereomers of each other. The isomers were labeled as they eluted off the silica gel column. The first isomer that eluted off was named isomer 1 and then isomers 2, 3 and lastly isomer 4.

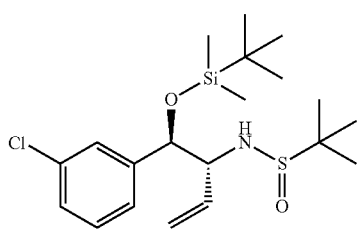

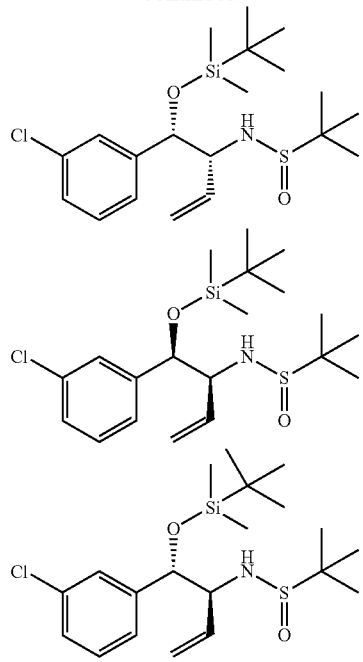

Isomer 1: m/z (ES) 416, 418 (M, M+2)$^+$, 438, 440 (MNa, MNa+2)$^+$. $^1$HNMR (500 MHz, CDCl$_3$) δ: 7.32 (s, 1H), 7.30 (br d, J=7.5, 1H), 7.26 (br d, J=6.2 Hz, 2H), 7.22-7.18 (m, 1H), 5.60 (ddd, J=7.3, 10.3, 17.4 Hz, 1H), 5.15 (d, J=10.3 Hz, 1H), 5.00 (d, J=17.3 Hz, 1H), 4.57 (d, J=7.4 Hz, 1H), 3.98-3.94 (m, 2H), 1.64 (br s, 1H), 1.23 (s, 9H), 0.91 (s, 9H), 0.08 (s, 3H), −0.18 (s, 3H).

Isomer 2: m/z (ES) 416, 418 (M, M+2)$^+$, 438, 440 (MNa, MNa+2)$^+$. $^1$HNMR (500 MHz, CDCl$_3$) δ: 7.33-7.31 (m, 2H), 7.26 (br d, J=5.0 Hz, 2H), 7.20-7.16 (m, 1H), 5.44 (ddd, J=7.2, 10.0, 17.4 Hz, 1H), 5.26 (overlapping d, J=7.3 Hz, 1H), 5.25 (overlapping d, J=17.3 Hz, 1H), 4.84 (d, J=4.4 Hz, 1H), 4.02 (dt, J=4.4, 7.8 Hz, 1H), 3.80 (d, J=4.4 Hz, 1H), 1.20 (s, 9H), 0.94 (s, 9H), 0.14 (s, 3H), −0.12 (s, 3H).

Isomer 3: m/z (ES) 416, 418 (M, M+2)$^+$, 438, 440 (MNa, MNa+2)$^+$. $^1$HNMR (500 MHz, CDCl$_3$) δ: 7.32-7.29 (m, 2H), 7.26-7.24 (m, 2H), 7.22-7.20 (m, 1H), 6.04 (ddd, J=7.1, 10.4, 17.4 Hz, 1H), 5.40 (d, J=10.2 Hz, 1H), 5.32 (d, J=17.3 Hz, 1H), 4.80 (d, J=4.0 Hz, 1H), 3.88-3.80 (m, 1H), 3.55 (d, J=9.4 Hz, 1H), 1.09 (s, 9H), 0.95 (s, 9H), 0.09 (s, 3H), −0.10 (s, 3H).

Isomer 4: m/z (ES) 416, 418 (M, M+2)$^+$, 438, 440 (MNa, MNa+2)$^+$. $^1$HNMR (500 MHz, CDCl$_3$) δ: 7.32 (s, 1H), 7.30 (br d, J=7.5, 1H), 7.27-7.25 (m, 2H), 7.21-7.18 (m, 1H), 5.92 (ddd, J=7.1, 10.3, 17.4 Hz, 1H), 5.23 (d, J=10.4 Hz, 1H), 5.18 (d, J=17.4 Hz, 1H), 4.75 (d, J=4.2 Hz, 1H), 3.88-3.82 (m, 1H), 3.33 (d, J=9.4 Hz, 1H), 1.19 (s, 9H), 0.94 (s, 9H), 0.09 (s, 3H), −0.14 (s, 3H).

Step F: ((1R)-1-[(R)-{[tert-butyl(dimethyl)silyl]oxy) (3-chlorophenyl)methyl]prop-2-en-1-yl}carbamate (i-2)

To isomer 1 (510 mg, 2.22 mmol) of N-{1-[{[tert-butyl (dimethyl)silyl]oxy}(3-chlorophenyl)methyl]-prop-2-en-1-yl}2-methylpropane-2-sulfinamide (from Step E) was added 5 mL anhydrous 4 M HCl in dioxane and the solution stirred for 15 min at room temperature. The reaction was concentrated to dryness and azeotroped with toluene (2×5 mL) to remove excess HCl. The residue was then taken up in anhydrous dichloromethane, set under nitrogen atmosphere, cooled to 0° C. with ice/water bath and then benzyl chloroformate (0.32 mL, 2.22 mmol) was slowly added via syringe followed by diisopropylethyl amine (1.19 mL, 6.66 mmol) and the resulting solution stirred for 2 h at 0° C. The solution was concentrated to dryness under vacuum and the residue was purified via preparative plates (4×1000 μM) eluding with 20% ethyl acetate in hexane to afford the title compound (703 mg, 71%). m/z (ES) 446, 448 (M, M+2)+, 468, 470 (MNa, MNa+2)+. $^1$HNMR (500 MHz, CDCl$_3$) δ: 7.32 (s, 1H), 7.30 (br d, J=7.5, 1H), 7.27-7.25 (m, 2H), 7.21-7.18 (m, 1H), 5.92 (ddd, J=7.1, 10.3, 17.4 Hz, 1H), 5.23 (d, J=10.4 Hz, 1H), 5.18 (d, J=17.4 Hz, 1H), 4.75 (d, J=4.2 Hz, 1H), 3.88-3.82 (m, 1H), 3.33 (d, J=9.4 Hz, 1H), 1.19 (s, 9H), 0.94 (s, 9H), 0.09 (s, 3H), −0.14 (s, 3H).

Intermediates related to those described above of varying stereochemistry may be prepared from the appropriate starting materials using the procedure described above.

i-2b

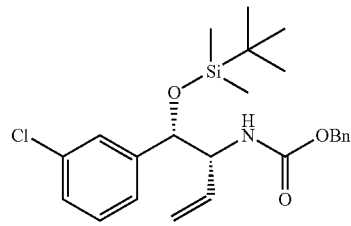

i-2c

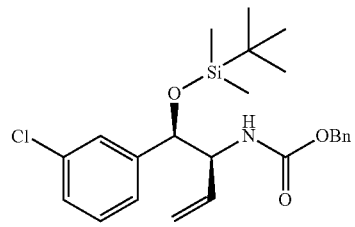

i-2d

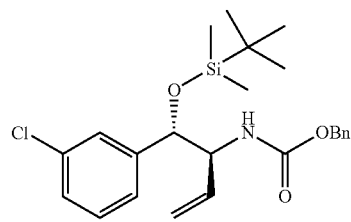

Intermediate 3

Tert-butyl(5R)-2-(4-aminobenzyl)-5-[(R)-{[tert-butyl(dimethyl)silyl]oxy}(phenyl)methyl]pyrrolidine-1-carboxylate (i-3)

i-3

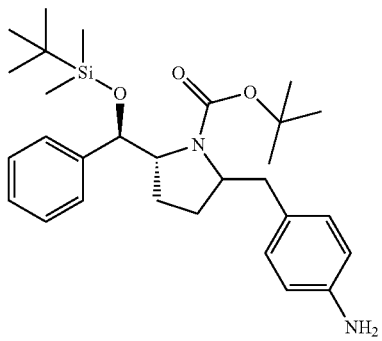

Step A: Benzyl{4-[(3E,5R,6R)-5-{[(benzyloxy)carbonyl]amino-6-{[tert-butyl(dimethyl)silyl]oxy}-6-(3-chlorophenyl)-2-oxohex-3-en-1-yl]phenyl}carbamate

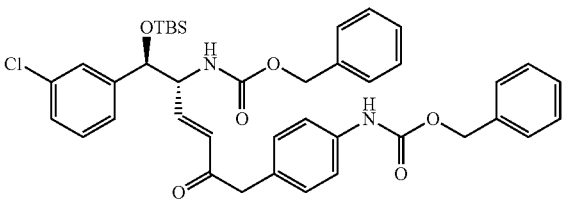 [SMILES: CC(C)(C)[Si](C)(C)O[C@H](c1cccc(Cl)c1)[C@@H](/C=C/C(=O)Cc1ccc(NC(=O)OCc2ccccc2)cc1)NC(=O)OCc1ccccc1]

To a solution of benzyl[3-(2-oxobut-3-en-1-yl)phenyl]carbamate (i-1) (820 mg, 2.80 mmol) and ((1R)-1-[(R)-{[tert-butyl(dimethyl)silyl]oxy)(3-chlorophenyl)methyl]prop-2-en-1-yl}carbamate (i-2) (500 mg, 1.12 mmol) in 7 mL of anhydrous dichloromethane was added the Zhan I catalyst (740 mg, 1.12 mmol) and the resulting green solution was heated to 40° C. overnight under nitrogen atmosphere. The reaction was concentrated to dryness and the residue purified via preparative plates (4×1000 μM) eluting with 40% ethyl acetate in hexane to afford the title compound (348 mg, 50%). m/z (ES) 713, 715 (M, M+2)+, 735, 737 (MNa, MNa-1-2)+.

Step B: 4-({(5R)-5-[(R)-([tert-butyl(dimethyl)silyl]oxy}(phenyl)methyl]pyrrolidin-2-yl}methyl)aniline

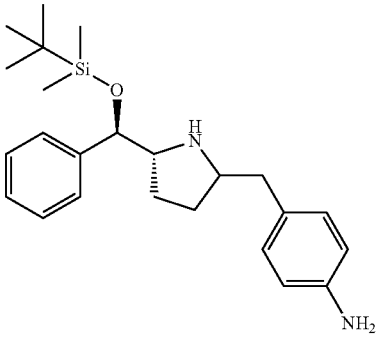

To a solution of 328 mg (0.46 mmol) of benzyl{4-[(3E,5R,6R)-5-{[(benzyloxy)carbonyl]amino-6-{[tert-butyl(dimethyl)silyl]oxy}-6-(3-chlorophenyl)-2-oxohex-3-en-1-yl]phenyl}carbamate (from Step A) in 25 mL ethanol was added 10% palladium on carbon and the suspension was set under hydrogen atmosphere via a balloon of hydrogen gas. The reaction was stirred under hydrogen for 1 h at room temperature. TLC proved that the reaction was complete. The catalyst was filtered off using a Gilmen 0.45 μM PTFE syringe filter and washed with ethanol (4×5 mL). The filtrate was concentrated to dryness under vacuum and the residue purified by preparative plate (3×1000 μM) eluding with 5% methanol in dichloromethane to afford the title compound (121 mg, 66%). m/z (ES) 397 (MH)+.

Step C: Tert-butyl(5R)-2-(4-aminobenzyl)-5-[(R)-{[tert-butyl(dimethyl)silyl]oxy}(phenyl)methyl]pyrrolidine-1-carboxylate (i-3)

To a solution of 121 mg (0.315 mmol) of 4-({(5R)-5-[(R)-([tert-butyl(dimethyl)silyl]oxy}(phenyl)methyl]pyrrolidin- 2-yl}methyl)aniline in 5 mL of anhydrous THF (from Step B) was added tert-butyl carbonate (69 mg, 0.315 mmol), followed by TEA (44 μL, 0.315 mmol) and the resulting solution stirred at room temperature under nitrogen atmosphere overnight. The reaction mixture was put directly on a preparative plate (1500 μM) and eluted with 30% ethyl acetate in hexane to afford the title compound (100 mg, 64%). m/z (ES) 497 (MH)$^+$, 397 (M-Boc)$^+$. $^1$HNMR (500 MHz, CDCl$_3$) δ: 7.40-7.30 (m, 5H), 6.75-6.68 (m, 2H), 6.56-6.51 (m, 2H), 5.52-5.48 (m, 1H), 5.32-5.28 (m, 1H), 4.16-4.06 (m, 2H), 3.88-3.82 (m, 1H), 3.76-3.70 (m, 1H), 3.55-3.48 (m, 2H), 2.74 (br d, J=11.8 Hz, 1H), 2.44 (br d, J=11.8 Hz, 1H), 2.05-1.94 (m, 1H), 1.90-1.82 (m, 1H), 1.60 (s, 9H), 1.50-1.42 (m, 1H), 1.32-1.22 (m, 2H), 1.10-1.02 (m, 1H), 0.95 (s, 9H), 0.08 (s, 3H), −0.15 (s, 3H).

Separation of Intermediate 4a and Intermediate 4b

Tert-butyl(2S,5R)-2-(4-aminobenzyl)-5-[(R)-{[tert-butyl(dimethyl)silyl]oxy}(phenyl)methyl]pyrrolidine-1-carboxylate (i-4a)

Tert-butyl(2R,5R)-2-(4-aminobenzyl)-5-[(R)-{[tert-butyl(dimethyl)silyl]oxy}(phenyl)methyl]pyrrolidine-1-carboxylate (i-4b)

lidine-1-carboxylate (4:1 mixture of cis and trans) was taken up in methanol and purified via the Berger Multigram SFC (supercritical) using an eluent of 30% methanol:60% carbon dioxide to separate the two diastereomers. The first isomer of the column was labeled minor isomer 1 and the second isomer was labeled major isomer 2.

i-4a: m/z (ES) 497 (MH)$^+$, 397 (M-Boc)$^+$. $^1$HNMR (500 MHz, CDCl$_3$) δ: 7.40-7.30 (m, 5H), 6.75-6.68 (m, 2H), 6.56-6.51 (m, 2H), 5.52-5.48 (m, 1H), 5.32-5.28 (m, 1H), 4.16-4.06 (m, 2H), 3.88-3.82 (m, 1H), 3.76-3.70 (m, 1H), 3.55-3.48 (m, 2H), 2.74 (br d, J=11.8 Hz, 1H), 2.44 (br d, J=11.8 Hz, 1H), 2.05-1.94 (m, 1H), 1.90-1.82 (m, 1H), 1.60 (s, 9H), 1.50-4.42 (m, 1H), 1.32-1.22 (m, 2H), 1.10-1.02 (m, 1H), 0.95 (s, 9H), 0.92 (d, 11.8 Hz, 1H), 0.12 (br d, J=14.0 Hz, 3H), −0.04 (s, 3H). Eluted 8.70 min on SFC, isomer 2 i-4b: m/z (ES) 497 (MH)$^+$, 397 (M-Boc)$^+$. $^1$HNMR (500 MHz, CDCl$_3$) δ: 7.40-7.30 (m, 5H), 6.76-6.68 (m, 2H), 6.56-6.51 (m, 2H), 5.52-5.48 (m, 1H), 5.32-5.28 (m, 1H), 4.16-4.06 (m, 2H), 3.88-3.82 (m, 1H), 3.76-3.70 (m, 1H), 3.60-3.46 (m, 2H), 2.72 (br d, J=12.0 Hz, 1H), 2.44 (br d, J=122 Hz, 1H), 2.05-1.94 (m, 1H), 1.90-1.82 (m, 1H), 1.64 (s, 9H), 1.50-1.42 (m, 1H), 1.32-1.22 (m, 2H), 1.10-1.02 (m, 1H), 0.95 (s, 9H), 0.14 (br d, J=13.8 Hz, 3H), 0.09 (s, 3H). Eluted 7.78 min on SFC, isomer 1.

Synthesis of Intermediate 4a and Intermediate 4b

Tert-butyl(2S,5R)-2-(4-aminobenzyl)-5-[(R)-{[tert-butyl(dimethyl)silyl]oxy}(phenyl)methyl]pyrrolidine-1-carboxylate (i-4a)

Tert-butyl(2R,5R)-2-(4-aminobenzyl)-5-[(R)-{[tert-butyl(dimethyl)silyl]oxy}(phenyl)methyl]pyrrolidine-1-carboxylate (i-4b)

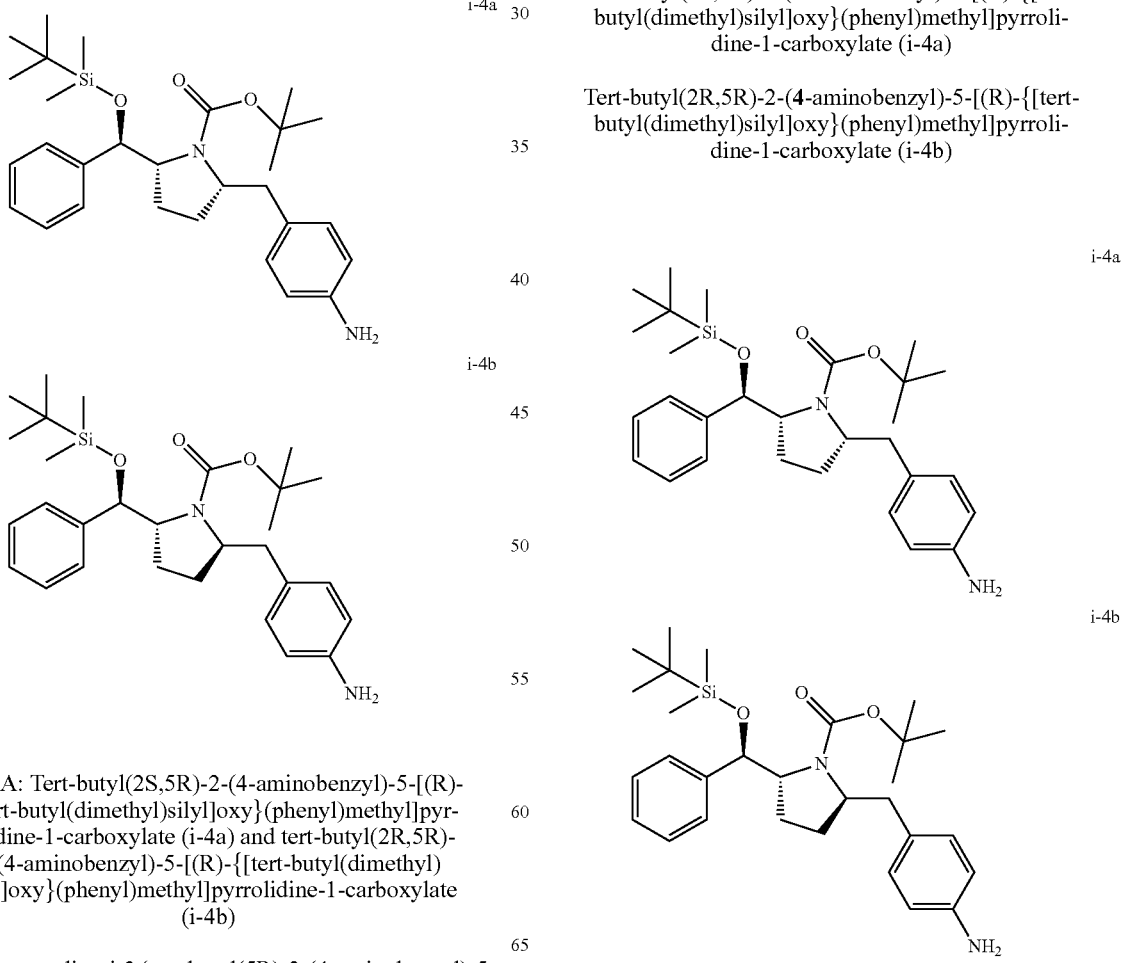

Step A: Tert-butyl(2S,5R)-2-(4-aminobenzyl)-5-[(R)-{[tert-butyl(dimethyl)silyl]oxy}(phenyl)methyl]pyrrolidine-1-carboxylate (i-4a) and tert-butyl(2R,5R)-2-(4-aminobenzyl)-5-[(R)-{[tert-butyl(dimethyl)silyl]oxy}(phenyl)methyl]pyrrolidine-1-carboxylate (i-4b)

The intermediate i-3 (tert-butyl(5R)-2-(4-aminobenzyl)-5-[(R)-{[tert-butyl(dimethyl)silyl]oxy}(phenyl)methyl]pyrro-

Step A: (4S)-3-Hex-5-ynoyl-4-phenyl-1,3-oxazolidin-2-one

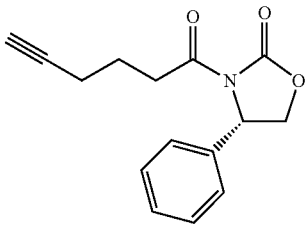 [SMILES: C#CCCCC(=O)N1C(=O)OC[C@@H]1c1ccccc1]

To a solution of 69.0 g (615 mmol) of 5-hexynoic acid and 214 mL (1540 mmol) of triethylamine in 1.0 L of anhydrous tetrahydrofuran at −25° C. under an atmosphere of nitrogen was added 83.0 mL (677 mmol) of trimethylacetyl chloride over 20 min. Upon addition a white precipitate formed and the resulting suspension was stirred for 2 h. Next, 28.7 g (677 mmol) of anhydrous lithium chloride and 100.0 g (615.0 mmol) of (4S)-4-phenyl-1,3-oxazolidin-2-one were added sequentially and the mixture was allowed to gradually warm to ambient temperature over 12 h. All volatiles were removed in vacuo and the residue was diluted with water (1 L) and extracted with ethyl acetate (3×300 mL). The combined organic layers were washed with brine (250 mL), dried over magnesium sulfate, filtered and concentrated in vacuo. The crude residue was purified by silica gel chromatography eluting with a 5-50% ethyl acetate in hexanes gradient to afford the title compound as a colorless solid (135 g, 85.4%). $^1$HNMR (500 MHz, CDCl$_3$): δ 7.40-7.37 (m, 2H), 7.36-7.32 (m, 1H), 7.31-7.28 (m, 2H), 5.42 (dd, J=8.9, 3.7 Hz, 1H), 4.69 (t, J=8.9 Hz, 1H), 4.28 (dd, J=9.2, 3.7 Hz, 1H), 3.13-3.02 (m, 2H), 2.24-2.21 (m, 2H), 1.94 (t, J=2.6 Hz, 1H), 1.84 (quintet, J=7.1 Hz, 2H). LC-MS: m/z (ES) 258.2 (MH)$^+$.

Step B: (4S)-3-{(2R)-2-[(S)-Hydroxy(phenyl)methyl]hex-5-ynoyl}-4-phenyl-1,3-oxazolidin-2-one

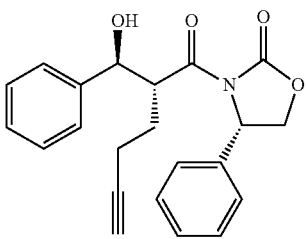 [SMILES: C#CCC[C@@H](C(=O)N1C(=O)OC[C@@H]1c1ccccc1)[C@H](O)c1ccccc1]

To a stirred solution of 56.8 g (221 mmol) of (4S)-3-hex-5-ynoyl-4-phenyl-1,3-oxazolidin-2-one from step A above in 265 mL of anhydrous ethyl acetate at ambient temperature under an atmosphere of nitrogen was added 6.31 g (66.2 mmol) of anhydrous magnesium chloride, 61.5 mL (442 mmol) of triethylamine, 26.9 mL (265 mmol) of benzaldehyde and 42.3 mL (331 mmol) of chlorotrimethylsilane and the resulting mixture was stirred for 72 h. The heterogeneous reaction mixture was filtered through a 300 mL plug of silica gel eluting with an additional 1 L of ethyl acetate. The filtrate was evaporated to dryness in vacuo and the residue suspended in 265 mL of methanol and 10 mL of trifluoroacetic acid. The resulting mixture was stirred at ambient temperature under nitrogen for 5 h during which time the reaction became homogeneous. All volatiles were then removed in vacuo and the residue was purified by silica gel chromatography eluting with a 5-15% ethyl acetate in hexanes gradient to afford the title compound as a white solid (65.0 g, 81.2%). $^1$H NMR (500 MHz, CDCl$_3$): δ 7.30-7.28 (m, 8H), 7.09-7.07 (m, 2H), 5.42 (dd, J=8.7, 3.7 Hz, 1H), 4.76-4.72 (m, 1H), 4.72-4.67 (m, 1H), 4.65 (t, J=8.7 Hz, 1H), 4.18 (dd, J=8.7, 3.7 Hz, 1H), 3.05 (d, J=7.8 Hz, 1H), 2.24 (td, J=7.1, 2.5 Hz, 2H), 2.00-1.93 (m, 2H), 1.67-1.61 (m, 1H). LC-MS: m/z (ES) 346.1 (MH-H$_2$O)$^+$, 386.0 (MNa)$^+$.

Step C: (2R)-2-[(S)-Hydroxy(phenyl)methyl]hex-5-ynoic acid

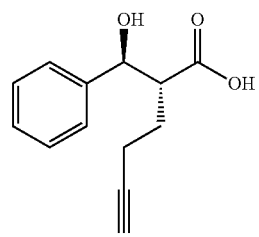 [SMILES: C#CCC[C@@H](C(=O)O)[C@H](O)c1ccccc1]

To a stirred solution of 65.0 g (179 mmol) of (4S)-3-{(2R)-2-[(S)-hydroxy(phenyl)methyl]hex-5-ynoyl}-4-phenyl-1,3-oxazolidin-2-one from Step B above in 1050 mL of a 20 to 1 mixture of anhydrous tetrahydrofuran to water at 0° C. under an atmosphere of nitrogen was added 77.0 mL (894 mmol) of a 35% aqueous hydrogen peroxide solution at a rate slow enough to keep the internal temperature below 3° C. Next, 395 mL (395 mmol) of a 1.0 M aqueous lithium hydroxide solution was added at a rate slow enough to keep the internal temperature of the reaction below 5° C. and the resulting mixture was stirred for 3 h at 0° C. The reaction was quenched with 755 mL (984 mmol) of a 1.3 M aqueous sodium sulfite solution at a rate slow enough to keep the internal temperature of the mixture below 5° C. All volatiles were removed in vacuo and the remaining aqueous phase was extracted with ethyl acetate (3×200 mL). The aqueous phase was then cooled to 0° C. and acidified with a 6 M aqueous hydrogen chloride solution until a pH of 3 was achieved. The aqueous phase was then extracted with ethyl acetate (3×300 mL) and the combined organics were washed with brine (100 ml), dried over magnesium sulfate, filtered and evaporated in vacuo. The residue was purified by silica gel chromatography eluting with a 5-10% ethyl acetate and 3% acetic acid in hexanes gradient to afford the title compound as a colorless gum (32.0 g, 82.0%). $^1$H NMR (500 MHz, CDCl$_3$): δ 7.39-7.28 (m, 5H), 4.85 (d, J=8.2, 1H), 3.03-2.97 (m, 1H), 2.29-2.15 (m, 2H), 1.97 (t, J=2.5 Hz, 1H), 1.93-1.82 (m, 1H), 1.62-1.55 (m, 1H). LC-MS: m/z (ES) 201.0 (MH-H$_2$O)$^+$.

Step D: (2R)-2-[(S)-{[Tert-butyl(dimethyl)silyl]oxy}(phenyl)methyl]hex-5-ynoic acid

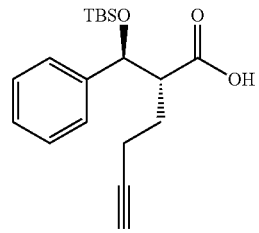 [SMILES: C#CCC[C@@H](C(=O)O)[C@H](O[Si](C)(C)C(C)(C)C)c1ccccc1]

To a stirred solution of 32.0 g (147 mmol) of (2R)-2-[(S)-hydroxy(phenyl)methyl]hex-5-ynoic acid from Step C above in 500 mL of anhydrous acetonitrile at ambient temperature under an atmosphere of nitrogen was added 77.0 mL (513 mmol) of 1,8-diazabicyclo[5.4.0]undec-7-ene 22 mL followed by 66.3 g (440 mmol) of tert-butyldimethylsilyl chloride in three portions over 10 min. The reaction mixture was stirred for 4 h then evaporated in vacuo to remove all volatiles. The residue was diluted with 300 mL of dichloromethane and 100 mL of water. A 1.0 M aqueous hydrogen chloride solution was added to the mixture until a pH of 3 was achieved in the aqueous layer. The phases were separated and the aqueous phase was extracted with dichloromethane (2×100 mL). The combined organics were washed with water (50 mL), brine (50 mL) then dried over magnesium sulfate. After filtration and evaporation in vacuo the residue was dissolved in 350 mL of methanol and 350 mL (280 mmol) of a 0.8 M aqueous potassium carbonate solution was added. The resulting mixture was stirred for 1.5 h then evaporated in vacuo to remove all volatiles. The residue was diluted with 300 mL of dichloromethane and the aqueous phase was acidified with a 5.0 M aqueous hydrogen chloride solution until a pH of 3 was achieved. The phases were separated and the aqueous phase was extracted with dichloromethane (2×100 mL). The combined organics were washed with water (50 mL), brine (50 mL) then dried over magnesium sulfate, filtered and evaporated in vacuo. The residue was purified by silica gel chromatography eluting with a 3-15% ethyl acetate in hexanes gradient to afford the title compound as a colorless solid (42.3 g, 86.6%). $^1$H NMR (500 MHz, CDCl$_3$): δ 7.36-7.27 (m, 5H), 4.78 (d, J=8.7, 1H), 2.90-2.86 (m, 1H), 2.19-2.11 (m, 1H), 2.10-2.03 (m, 1H), 1.90 (t, J=2.6 Hz, 1H), 1.75-1.67 (m, 1H), 1.41-1.34 (m, 1H), 0.83 (s, 9H), 0.02 (s, 3H), −0.27 (s, 3H). LC-MS: m/z (ES) 333.2 (MH)$^+$.

Step E: 4-Methoxybenzyl {(1R)-1-[(R)-{[tert-butyl(dimethyl)silyl]oxy}(phenyl)methyl]pent-4-yn-1-yl}carbamate

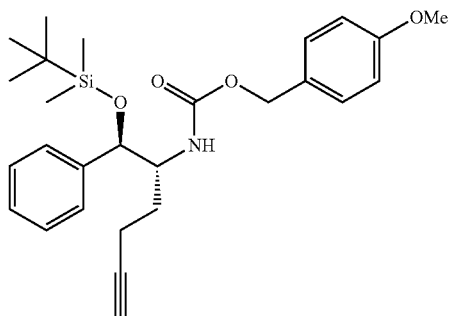 [SMILES: C#CCC[C@@H](NC(=O)OCc1ccc(OC)cc1)[C@H](O[Si](C)(C)C(C)(C)C)c1ccccc1]

To a solution of 40.0 g (120 mmol) of (2R)-2-[(S)-{[tert-butyl(dimethyl)silyl]oxy}(phenyl)methyl]hex-5-ynoic acid from Step D above and 33.5 mL (241 mmol) of triethylamine in 400 mL of anhydrous toluene at ambient temperature under an atmosphere of nitrogen was added 37.5 mL (132 mmol) of diphenylphosphoryl azide. The mixture was stirred for 5 h and then 37.5 mL (301 mmol) of 4-methoxybenzyl alcohol was added. The resulting mixture was heated to 105° C. for 16 h, cooled to ambient temperature and then diluted with 250 mL of a saturated aqueous bicarbonate solution. The phases were separated and the aqueous phase was extracted with ethyl acetate (2×150 mL). The combined organics were washed with water (100 mL), brine (100 mL) then dried over magnesium sulfate, filtered and evaporated in vacuo. The crude residue was purified by silica gel chromatography eluting with 3-10% ethyl acetate in hexanes to afford the title compound as a colorless oil (50.9 g, 90.5%). $^1$H NMR (500 MHz, CDCl$_3$): 7.28-7.21 (m, 7H), 6.87 (d, J=8.4 Hz, 2H), 4.92 (s, 2H), 4.77-4.59 (m, 2H), 3.89-3.84 (m, 1H), 3.81 (s, 3H), 2.30-2.22 (m, 2H), 1.95 (m, 1H), 1.91-1.85 (m, 1H), 1.57-1.50 (m, 1H), 0.89 (s, 9H), 0.06 (s, 3H), −0.15 (s, 3H). LC-MS: m/z (ES) 468.1 (MH)$^+$, 490.0 (MNa)$^+$.

Step F: 4-methoxybenzyl[(R)-1-[(R)-{[tert-butyl(dimethyl)silyl]oxy}(phenyl)methyl]-5-(4-nitrophenyl)pent-4-yn-1-yl]carbamate

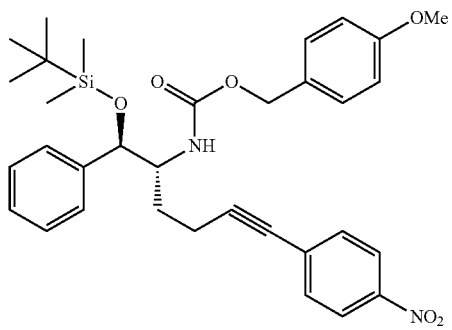 [SMILES: COc1ccc(COC(=O)N[C@H](CCC#Cc2ccc([N+](=O)[O-])cc2)[C@H](O[Si](C)(C)C(C)(C)C)c2ccccc2)cc1]

To a solution of acetylene (from Step E, 40 g, 80 mmol) and 4-iodonitrobenzene (21.8 g, 88 mmol) in anhydrous DMF (500 ml) was added triethylamine (111 mL, 797 mmol). Pd(dppf)Cl$_2$ (1.95 g, 2.39 mmol) and copper(I) iodide (910 mg, 4.78 mmol) was added and the mixture degassed with nitrogen (bubble 15 min) and the resulting solution stirred at room temperature for 5 h. The mixture was poured into water (1200 m) and extracted with EtOAc (3×300 mL). The combined organics were then washed with water (2×500 mL), sat. NaCl (200 mL), dried over magnesium sulfate, filtered and evaporated under vacuum. Residue was purified by MPLC (Horizon Biotage 2× Flash 65i) eluting with a gradient of 0-30% ethyl acetate in hexane to give 41 g (84%) as a dark red oil. %). $^1$H NMR (500 MHz, CDCl$_3$): 8.11-8.04 (m, 2H), 7.94-8.01 (m, 1H), 7.38-7.21 (m, 8H), 6.87 (d, J=8.4 Hz, 2H), 4.98 (s, 2H), 4.77-4.59 (m, 2H), 4.00-3.95 (m, 3H), 3.81 (s, 3H), 2.56 (t, J=7.1 Hz, H=2H), 2.00-1.95 (m, 1H), 1.66-1.61 (m, 1H), 0.93 (s, 9H), 0.10 (s, 3H), −0.10 (s, 3H). LC-MS: m/z (ES) 589.3 (MH)$^+$, 611.2 (MNa)$^+$.

Step G: 4-methoxybenzyl[(1R)-1-[(R)-{[tert-butyl(dimethyl)silyl]oxy}(phenyl)methyl]-5-(4-nitrophenyl)-4-oxopentyl]carbamate

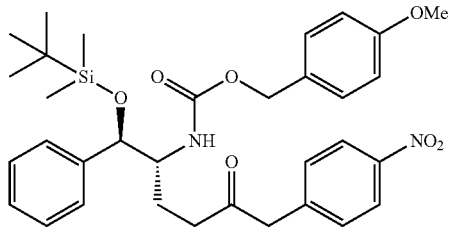 [SMILES: COc1ccc(COC(=O)N[C@H](CCC(=O)Cc2ccc([N+](=O)[O-])cc2)[C@H](O[Si](C)(C)C(C)(C)C)c2ccccc2)cc1]

To a solution of nitrophenyl acetylene (from Step F, 41 g, 65.5 mmol) in DMF (40 ml) was added pyrrolidine (14 mL, 196.5 mmol) and the resulting mixture heated at 80° C. for 3 h. The mixture was cooled to room temperature and a 10% solution of acetic acid in water (110 ml) was added, and the resulting solution stirred at room temperature for another 3 h. The mixture was poured into water (300 ml) and extracted with EtOAc (3×250 ml); combined EtOAc layers were washed with water (2×250 ml), sat. NaCl (100 ml), dried over MgSO$_4$, filtered and evaporated. The residue was purified by Horizon Flash 75 eluting with a gradient rising from 100% Hexanes to 50% EtOAc in Hexanes to give 34 g (81%) as a dark orange oil. $^1$H NMR (500 MHz, CDCl$_3$): 8.17-8.14 (m, 2H), 7.32-7.23 (m, 9H), 6.87 (d, J=8.4 Hz, 2H), 4.96 (d, J=12.2 Hz, 1H), 4.90 (d, J=12.1 Hz, 1H), 4.72 (d, J=3 Hz, 1H), 4.16-4.13 (m, 1H), 3.81 (s, 3H), 3.71-3.77 (m, 2H), 2.65-2.52 (m, 2H), 1.97-1.92 (m, 1H), 1.72-1.60 (m, 1H), 0.93 (s, 9H), 0.05 (s, 3H), −0.13 (s, 3H).

Step H: (2R,5S)-2-[(R)-{[tert-butyl(dimethyl)silyl]oxy}(phenyl)methyl]-5-(4-nitrobenzyl)pyrrolidine (2R,5R)-2-[(R)-{[tert-butyl(dimethyl)silyl]oxy}(phenyl)methyl]-5-(4-nitrobenzyl)pyrrolidine isomer 1

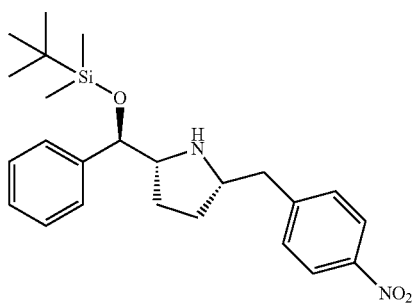

isomer 2

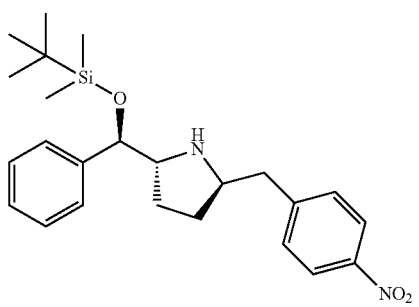

To a solution of MOZ protected ketone amine (from Step G, 34 g, 56 mmol) in DCM (350 ml) was added TFA (256 ml) and the resulting mixture stirred at room temperature for 1.5 h. The solution was evaporated under vacuum and residue partitioned between DCM and sat. NaHCO$_3$. The organic layer was dried over MgSO$_4$, filtered and evaporated. The residue was dissolved in MeOH (750 ml) and cooled to 0° C. via ice/water bath. Sodium cyanoborohydride (21.2 g, 337 mmol) was then added and the resulting mixture was stirred overnight to allow to warm to room temperature. The mixture was quenched by addition of water and the organics removed under vacuum. The aqueous layer was then extracted with EtOAc (×2) and the combined EtOAc layers washed with sat. NaCl, dried over MgSO$_4$, filtered and evaporated under vacuum. The residue was purified by column chromatography on silica (eluent: gradient rising from 100% Hexanes to 35% EtOAc in Hexanes) to give 16.4 g (63.4%) of the first isomer, (2R,5S)-2-[(R)-{[tert-butyl(dimethyl)silyl]oxy}(phenyl)methyl]-5-(4-nitrobenzyl)pyrrolidine, and 3.1 g (12%) of the second isomer (2R,5R)-2-[(R)-{[tert-butyl(dimethyl)silyl]oxy}(phenyl)methyl]-5-(4-nitrobenzyl)pyrrolidine.

Isomer 1: LC-MS: m/z (ES) 427.3 (MH)$^+$
Isomer 2: LC-MS: m/z (ES) 427.3 (MH)$^+$ Step I: Tert-butyl(2R,5S)-2-[(R)-{[tert-butyl(dimethyl)silyl]oxy}(phenyl)methyl]-5-(4-nitrobenzyl)pyrrolidine-1-carboxylate

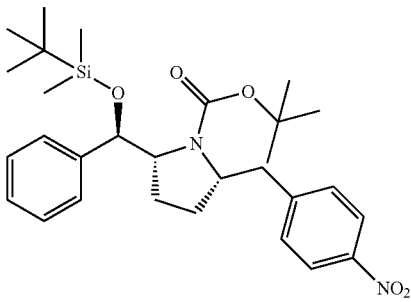 [SMILES: CC(C)(C)OC(=O)N1[C@H](Cc2ccc([N+](=O)[O-])cc2)CC[C@@H]1[C@H](O[Si](C)(C)C(C)(C)C)c1ccccc1]

To a solution of tert-butyl(2R,5S)-2-[(R)-{[tert butyl(dimethyl)silyl]oxy}(phenyl)methyl]-5-(4-nitrobenzyl)pyrrolidine-1-carboxylate (12 g, 42.5 mmol) in anhydrous THF was added Boc anhydride (9.3 g, 42.5 mmol) followed by TEA (17.76 mL, 127.4 mmol) and the resulting solution stirred at room temperature under nitrogen atmosphere for 2 h. The mixture was washed with water (100 mL) and extracted with ethyl acetate (2×200 mL). The organics were dried over sodium sulfate, filtered, and concentrated under vacuum. The residue was purified via Horizon Biotage MPLC (65i silica gel column) eluting with a gradient of 20-75% ethyl acetate in hexane to afford the desired product. LC-MS: m/z (ES) 527.3 (MH)$^+$, 549.2 (MNa)$^+$.

Step J: Tert-butyl(2R,5R)-2-[(R)-{[tert-butyl(dimethyl)silyl]oxy}(phenyl)methyl]-5-(4-nitrobenzyl)pyrrolidine-1-carboxylate

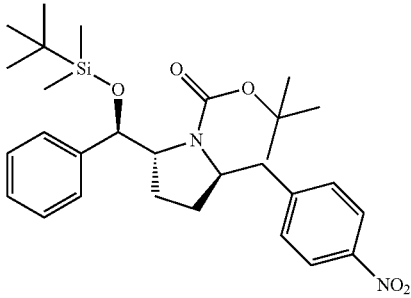

Prepared in the same manner as Step I but replacing the cis pyrrolidine isomer with the trans isomer, (2R,5R)-2-[(R)-{[tert-butyl(dimethyl)silyl]oxy}(phenyl)methyl]-5-(nitrobenzyl)pyrrolidine. LC-MS: m/z (ES) 527.3 (MH)$^+$, 549.2 (MNa)$^+$.

Step K: Tert-butyl(2S,5R)-2-(4-aminobenzyl)-5-[(R)-{[tert-butyl(dimethyl)silyl]oxy}(phenyl)methyl]pyrrolidine-1-carboxylate (i-4a)

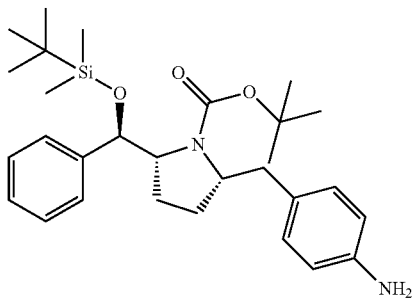

i-4a

A 500 mL parr shaker flask was charged with 10% Pd/c (4.75 g) and to this was added 100 mL of methanol to cover the catalyst. A solution of the nitro intermediate from Step (8.5 g, 18.5 mmol) in methanol (80 mL) was then added to the suspension, followed by 15.4 mL of 1.0 M hydrogen chloride in methanol solution. The reaction vessel was set under 50 PSI hydrogen gas and the mixture agitated overnight. An aliquot was taken and analyzed through the LC-MS which showed complete reaction.

The catalyst was filtered off using celite and washed with methanol (2×100 mL). The filtrate was concentrated to dryness and the product was purified via Horizon MPLC (65i silica column) eluting with a gradient rising from 0% to 30% ethyl acetate in hexane to afford the title compound (6.2 g, 72%). m/z (ES) 497 (MH)$^+$, 397 (M-Boc)$^+$. $^1$HNMR (500 MHz, CDCl$_3$) δ: 7.38-7.29 (m, 5H), 6.76-6.68 (m, 2H), 6.55-6.50 (m, 2H), 5.52-5.49 (m, 1H), 5.30-5.27 (m, 1H), 4.15-4.05 (m, 2H), 3.86-3.81 (m, 1H), 3.76-3.71 (m, 1H), 3.55-3.47 (m, 2H), 2.74 (br d, J=11.7 Hz, 1H), 2.44 (br d, J=11.7 Hz, 1H), 2.05-1.93 (m, 1H), 1.90-1.83 (m, 1H), 1.60 (s, 9H), 1.50-1.42 (m, 1H), 1.31-1.21 (m, 2H), 1.10-1.02 (m, 1H), 0.95 (s, 9H), 0.92 (d, J=11.8 Hz, 1H), 0.13 (br d, J=14.0 Hz, 3H), −0.05 (s, 3H)

Step L: Tert-butyl(2R,5R)-2-(4-aminobenzyl)-5-[(R)-{[tert-butyl(dimethyl)silyl]oxy}(phenyl)methyl]pyrrolidine-1-carboxylate (i-4b)

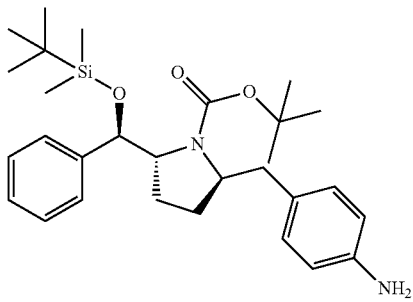 [SMILES: CC(C)(C)OC(=O)N1[C@@H](Cc2ccc([N+](=O)[O-])cc2)CC[C@@H]1[C@H](O[Si](C)(C)C(C)(C)C)c1ccccc1]

i-4b

Prepared in the same manner as Step K but replacing the cis pyrrolidine isomer with the trans isomer, Tert-butyl(2R,5R)-2-[(R)-{[tert-butyl(dimethyl)silyl]oxy}(phenyl)methyl]-5-(4-nitrobenzyl)pyrrolidine-1-carboxylate. m/z (ES) 497 (MH)$^+$, 397 (M-Boc)$^+$. $^1$HNMR (500 MHz, CDCl$_3$) δ: 7.41-7.30 (m, 5H), 6.73-6.67 (m, 2H), 6.56-6.50 (m, 2H), 5.52-5.48 (m, 1H), 5.33-5.28 (m, 1H), 4.15-4.06 (m, 2H), 3.86-3.81 (m, 1H), 3.76-3.70 (m, 1H), 3.59-3.46 (m, 2H), 2.72 (br d, J=12.0 Hz, 1H), 2.44 (br d, J=12.0 Hz, 1H), 2.05-1.93 (m, 1H), 1.90-1.82 (m, 1H), 1.64 (s, 9H), 1.49-1.42 (m, 1H), 1.32-1.20 (m, 2H), 1.10-1.02 (m, 1H), 0.95 (s, 9H), 0.14 (br d, J=13.7 Hz, 3H), 0.10 (s, 3H).

Intermediate 5

4-Methoxybenzyl{(1R)-1-[(R)-{[tert-butyl(dimethyl)silyl]oxy}(6-chloropyridin-3-yl)methyl]pent-4-yn-1-yl}carbamate (i-5)

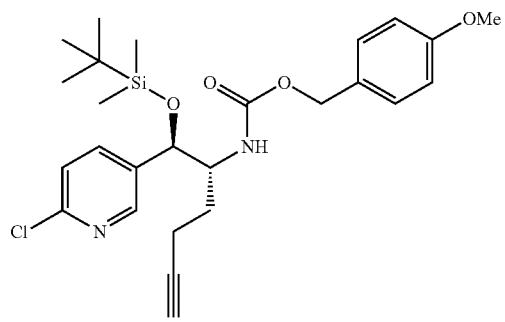 [SMILES: C#CCC[C@@H](NC(=O)OCc1ccc(OC)cc1)[C@H](O[Si](C)(C)C(C)(C)C)c1ccc(Cl)nc1]

Step A: (4S)-4-Benzyl-3-hex-5-ynoyl-1,3-oxazolidin-2-one

To a solution of 10 g (89 mmol) of 5-hexynoic acid and 31.0 mL (223 mmol) of triethylamine in 450 mL of anhydrous tetrahydrofuran at −25° C. under an atmosphere of nitrogen was added 12 mL (98 mmol) of trimethylacetyl chloride over 20 min. Upon addition a white precipitate formed and the resulting suspension was stirred for 2 h. Next, 4.2 g (98 mmol) of anhydrous lithium chloride and 17 g (94 mmol) of (S)-(−)-4-benzyl-2-oxazolidinone were added sequentially and the mixture was allowed to gradually warm to ambient temperature over 12 h. All volatiles were removed in vacuo and the residue was diluted with water (500 mL) and extracted with ether (3×200 mL). The combined organic layers were washed with brine (100 mL), dried over magnesium sulfate, filtered and concentrated in vacuo. The crude residue was purified by silica gel chromatography eluting with a 10-25% ethyl acetate in hexanes gradient to afford the title compound as a colorless solid (22 g, 93%). $^1$H NMR (500 MHz, CDCl$_3$): δ 7.35-7.31 (m, 2H), 7.28-7.25 (m, 1H), 7.19-7.21 (m, 2H), 4.69-4.64 (m, 1H), 4.22-4.15 (m, 2H), 3.28 (dd, J=13.4, 3.3 Hz, 1H), 3.13-3.01 (m, 2H), 2.78 (dd, J=13.4, 9.6 Hz, 1H), 2.34-2.30 (m, 2H), 1.99 (t, J=2.7 Hz, 1H), 1.96-1.88 (m, 2H). LC-MS: m/z (ES) 272.2 (MH)$^+$, 294.3 (MNa)$^+$.

Step B: (4S)-4-Benzyl-3-{(2R)-2-[(S)-(6-chloropyridin-3-yl)(hydroxy)methyl]hex-5-ynoyl}-1,3-oxazinan-2-one To a stirred solution of 23.0 g (837 mmol) of (4S)-4-benzyl-3-hex-5-ynoyl-1,3-oxazolidin-2-one from step A above in 200 mL of anhydrous ethyl acetate at ambient temperature under an atmosphere of nitrogen was added 1.6 g (17 mmol) of anhydrous magnesium chloride, 23.0 mL (166 mmol) of triethylamine, 14.0 g (100 mmol) of 6-chloropyridine-3-carboxaldehyde and 16.0 mL (124 mmol) of chlorotrimethylsilane and the resulting mixture was stirred for 72 h. The heterogeneous reaction mixture was filtered through a 300 mL plug of silica gel eluting with an additional 1 L of ethyl acetate. The filtrate was evaporated to dryness in vacuo and the residue suspended in 200 mL of methanol and 5.0 mL of trifluoroacetic acid. The resulting mixture was stirred at ambient temperature under nitrogen for 5 hours during which time the reaction became homogeneous. All volatiles were then removed in vacuo and the residue was purified by silica gel chromatography eluting with a 10-15% ethyl acetate in hexanes gradient to afford the title compound as a white solid (30 g, 88%). LC-MS: m/z (ES) 413.2 (MH)$^+$.

Step C: (4S)-4-Benzyl-3-{(2R)-2-[(S)-{[tert-butyl (dimethyl)silyl]oxy}(6-chloropyridin-3-yl)methyl] hex-5-ynoyl}-1,3-oxazinan-2-one To a stirred solution of 29.7 g (71.9 mmol) of (4S)-4-benzyl-3-{(2R)-2-[(S)-(6-chloropyridin-3-yl)(hydroxy)methyl]hex-5-ynoyl}-1,3-oxazinan-2-one from Step B above and 15.0 mL (126 mmol) of 2,6-lutidine in 300 mL of anhydrous dichloromethane at 0° C. under an atmosphere of nitrogen was added 22 mL (94 mmol) of tert-butyldimethylsilyl trifluoromethanesulfonate at a rate slow enough to keep the internal temperature below 3° C. The reaction mixture was stirred for 16 h at 0° C. then evaporated in vacuo to remove all volatiles. The residue was diluted with 400 mL of water and extracted with diethyl ether (3×300 mL). The combined organics were washed sequentially with a 0.5 M aqueous hydrochloric acid solution (100 mL), water (100 mL) brine (100 mL) then dried over magnesium sulfate. After filtration and evaporation in vacuo the residue was purified by silica gel chromatography eluting with a 5-8% ethyl acetate in hexanes gradient to afford the title compound as a colorless foam (37 g, 97%). LC-MS: m/z (ES) 527.3 (MH)$^+$.

Step D: (2R)-2-[(S)-{[Tert-butyl(dimethyl)silyl]oxy} (6-chloropyridin-3-yl)methyl]hex-5-ynoic acid To a stirred solution of 37 g (70 mmol) of (4S)-4-benzyl-3-{(2R)-2-[(S)-{[tert-butyl(dimethyl)silyl]oxy}(6-chloropyridin-3-yl)methyl]hex-5-ynoyl}-1,3-oxazinan-2-one from Step C above in 520 mL of a 3 to 1 mixture of anhydrous tetrahydrofuran to water at 0° C. under an atmosphere of nitrogen was added 30 mL (350 mmol) of a 35% aqueous hydrogen peroxide solution at a rate slow enough to keep the internal temperature below 3° C. Next, 140 mL (140 mmol) of a 1.0 M aqueous sodium hydroxide solution was added at a rate slow enough to keep the internal temperature of the reaction below 5° C. After complete addition the resulting mixture was stirred for 18 h at 0° C. then quenched with a solution of 350 mL (420 mmol) of a 1.2 M aqueous sodium sulfite solution at a rate slow enough to keep the internal temperature of the mixture below 15° C. All volatiles were removed in vacuo and the remaining aqueous phase was cooled to 0° C. and acidified with a 2.5 M aqueous hydrogen chloride solution until a pH of 3 was achieved. The aqueous phase was then extracted with ethyl acetate (3×200 mL) and the combined organics were washed with brine (10 ml), dried over magnesium sulfate, filtered and evaporated in vacuo. The residue was purified by silica gel chromatography eluting with 15% ethyl acetate and 3% acetic acid in hexanes to afford the title compound as a white solid (16 g, 62%). LC-MS: m/z (ES) 368.2 (MH)$^+$.

Step E: 4-Methoxybenzyl{(1R)-1-[(R)-{[tert-butyl (dimethyl)silyl]oxy}(6-chloropyridin-3-yl)methyl] pent-4-yn-1-yl}carbamate To a solution of 16 g (44 mmol) of (2R)-2-[(S)-{[tert-butyl (dimethyl)silyl]oxy}-(6-chloropyridin-3-yl)methyl]hex-5-ynoic acid from Step D above and 12 mL (87 mmol) of triethylamine in 150 mL of anhydrous toluene at ambient temperature under an atmosphere of nitrogen was added 10 mL (46 mmol) of diphenylphosphoryl azide. The mixture was stirred for 6 h and then 14.0 mL (109 mmol) of 4-methoxybenzyl alcohol was added. The resulting mixture was heated to 100° C. for 16 h, cooled to ambient temperature and then evaporated in vacuo to remove all volatiles. The crude residue was purified by silica gel chromatography eluting with 15% ethyl acetate in hexanes to afford the title compound (i-5) as a yellow foam (17 g, 78%). $^1$H NMR (500 MHz, CDCl$_3$): δ 8.28 (d, J=2.0 Hz, 1H), 7.53 (dd, J=8.2, 2.3 Hz, 1H), 7.22 (d, J=8.4 Hz, 2H), 7.18 (d, J=8.2 Hz, 1H), 6.90 (d, J=8.4 Hz, 2H), 4.96-4.89 (m, 2H), 4.82 (d, J=2.5 Hz, 1H), 4.74 (d, J=9.6 Hz, 1H), 3.90-3.84 (m, 1H), 3.82 (s, 3H), 2.30-2.26 (m, 2H), 1.97 (t, J=2.5 Hz, 1H), 1.89-1.83 (m, 1H), 1.58-1.52 (m, 1H), 0.89 (s, 9H), 0.08 (s, 3H), −0.12 (s, 3H). LC-MS: m/z (ES) 503.3 (MH)$^+$.

Intermediate 6 and Intermediate 7

5-{(R)-{[tert-butyl(dimethyl)silyl]oxy}[(2R,5S)-5-(4-nitrobenzyl)pyrrolidin-2-yl]methyl}-2-chloropyridine and 5-{(R)-{[tert-butyl(dimethyl)silyl]oxy} [(2R,5R)-5-(4-nitrobenzyl)pyrrolidin-2-yl]methyl}-2-chloropyridine

INTERMEDIATE 6

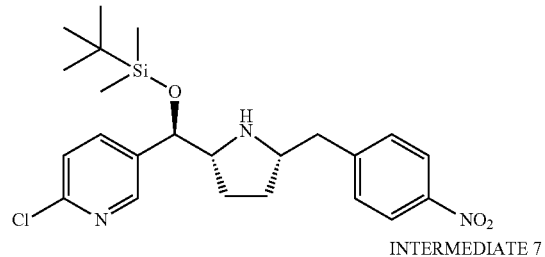

INTERMEDIATE 7

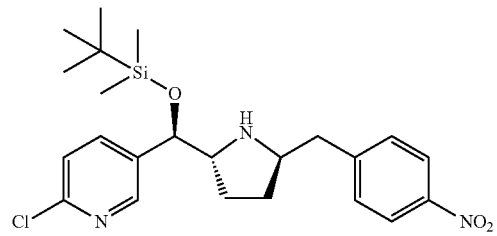

Step A: 4-Methoxybenzyl[(1R)-1-[(R)-{[tert-butyl (dimethyl)silyl]oxy}(6-chloropyridin-3-yl)methyl]-5-(4-nitrophenyl)pent-4-yn-1-yl]carbamate To a mixture of 9.2 g (37 mmol) of 4-iodonitrobenzene and 1.2 g (1.0 mmol) of tetrakis(triphenylphosphine)palladium (0) in 300 mL of anhydrous acetonitrile under an atmosphere of nitrogen was added copper(I) iodide 0.38 g (2.0 mmol). The resulting mixture was stirred at ambient temperature for 15 min then 16.8 g (33.4 mmol) of Intermediate 5 was added followed by 47.0 mL (334 mmol) of triethylamine. The reaction was stirred at ambient temperature for 15 h then evaporated to remove all volatiles. The residue was diluted with 100 mL of a saturated aqueous sodium bicarbonate solution and the aqueous suspension was extracted with diethyl ether (3×100 mL). The combined organic layers were washed with water (50 mL) and brine (50 ml), dried over magnesium sulfate, filtered and evaporated in vacuo. The residue was purified by silica gel chromatography eluting with 15% ethyl acetate in hexanes to afford the title compound as a yellow solid (18 g, 84%). LC-MS: m/z (ES) 624.4 (MH)$^+$.

Step B: 4-Methoxybenzyl[(1R)-1-[(R)-{[tert-butyl(dimethyl)silyl]oxy}(6-chloropyridin-3-yl)methyl]-5-(4-nitrophenyl)-4-oxopentyl]carbamate To 17.5 g (28.0 mmol) of 4-methoxybenzyl[(1R)-1-[(R)-{[tert-butyl(dimethyl)silyl]oxy}(6-chloropyridin-3-yl)methyl]-5-(4-nitrophenyl)pent-4-yn-1-yl]carbamate from Step A above in 100 mL of anhydrous N,N-dimethylformamide under an atmosphere of nitrogen was added 7.0 mL (84 mmol) of pyrrolidine. The resulting mixture was heated to 80° C. for 5 h. After cooling to ambient temperature, 5 mL of a 10% aqueous acetic acid solution was added and the resulting mixture stirred for 3 h. All volatiles were then removed in vacuo and the residue diluted with 500 mL of a saturated aqueous sodium bicarbonate solution and 200 mL of diethyl ether. The layers were separated and the aqueous phase extracted with diethyl ether (2×200 mL). The combined organic layers were washed with water (50 mL) then brine (50 ml), dried over magnesium sulfate, filtered and evaporated in vacuo to afford the title compound as a yellow gum (18 g, >99%) that was used without further purification. LC-MS: m/z (ES) 642.3 (MH)$^+$.

Step C: 5-{(R)-{[Tert-butyl(dimethyl)silyl]oxy}[(2R)-5-(4-nitrobenzyl)-3,4-dihydro-2H-pyrrolo-2-yl]methyl}-2-chloropyridine To a stirred solution of 18 g (28 mmol) of 4-methoxybenzyl[(1R)-1-[(R)-{[tert-butyl(dimethyl)silyl]oxy}(6-chloropyridin-3-yl)methyl]-5-(4-nitrophenyl)-4-oxopentyl]carbamate from Step B above in 75 mL of anhydrous dichloromethane was added 75 ml of trifluoroacetic acid. The resulting mixture was stirred at ambient temperature for 2 h during which time the reaction became dark red in color. All volatiles were removed in vacuo and the residue dissolved in 300 mL of dichloromethane. The solution was washed with a saturated aqueous sodium bicarbonate solution (2×100 mL), brine (100 ml) and then dried over magnesium sulfate and filtered. All volatiles were evaporated in vacuo to afford the title compound as a dark red gum (13 g, >99%) that was used immediately without further purification. LC-MS: m/z (ES) 460.4 (MH)$^+$.

Step D: 5-{(R)-{[tert-butyl(dimethyl)silyl]oxy}[(2R,5S)-5-(4-nitrobenzyl)pyrrolidin-2-yl]methyl}-2-chloropyridine and 5-{(R)-{[tert-butyl(dimethyl)silyl]oxy}[(2R,5R)-5-(4-nitrobenzyl)pyrrolidin-2-yl]methyl}-2-chloropyridine To a stirred suspension of 13 g (28 mmol) of 5-{(R)-{[tert-butyl(dimethyl)silyl]oxy}[(2R)-5-(4-nitrobenzyl)-3,4-dihydro-2H-pyrrol-2-yl]methyl}-2-chloropyridine from Step C above in 200 mL of anhydrous methanol at 0° C. under an atmosphere of nitrogen was added 12 g (190 mmol) of sodium cyanoborohydride and the resulting mixture was stirred for 6 h. The reaction mixture was quenched at 0° C. by slow addition of 150 mL of water followed by evaporation of all volatile organics in vacuo. The remaining aqueous phase was then extracted with ethyl acetate (3×150 mL) and the combined organic layers were washed with water (50 mL) then brine (50 ml), dried over magnesium sulfate, filtered and evaporated in vacuo. The crude residue was purified by silica gel chromatography eluting with a 5-10% acetone in hexanes gradient to afford the two title compounds.

First spot to elute (Intermediate 6—cis isomer): 5-{(R)-{[tert-butyl(dimethyl)silyl]oxy}[(2R,5S)-5-(4-nitrobenzyl)pyrrolidin-2-yl]methyl}-2-chloropyridine is a yellow gum (6.5 g, 50%): $^1$H NMR (500 MHz, CDCl$_3$): δ 8.31 (d, J=2.3 Hz, 1H), 8.13 (d, J=8.7 Hz, 2H), 7.62 (dd, J=8.2, 2.3 Hz, 1H), 7.36 (d, J=8.7 Hz, 2H), 7.27 (d, J=8.5 Hz, 1H), 4.45 (d, J=6.9 Hz, 1H), 3.32-3.27 (m, 1H), 3.19-3.14 (m, 1H), 2.83 (dd, J=13, 5.0 Hz, 1H), 2.72 (dd, J=13, 8.0 Hz, 1H), 1.90 (br s, 1H), 1.79-1.72 (m, 1H), 1.42-1.38 (m, 2H), 1.31-1.24 (m, 1H), 0.82 (s, 9H), 0.19 (s, 3H), −0.15 (s, 3H). LC-MS: m/z (ES) 462.5 (MH)$^+$.

Second spot to elute (Intermediate 7—trans isomer): 5-{(R)-{[tert-butyl-(dimethyl)silyl]oxy}[(2R,5R)-5-(4-nitrobenzyl)pyrrolidin-2-yl]methyl}-2-chloropyridine is a yellow gum (0.65 g, 5.0%): $^1$H NMR (500 MHz, CDCl$_3$): δ 8.26 (d, J=2.1 Hz, 1H), 8.15 (d, J=8.5 Hz, 2H), 7.60 (dd, J=8.2, 2.3 Hz, 1H), 7.36 (d, J=8.5 Hz, 2H), 7.28 (d, J=8.2 Hz, 1H), 4.31 (d, J=7.6 Hz, 1H), 3.38-3.30 (m, 2H), 2.86 (dd, J=13.2, 5.2 Hz, 1H), 2.73 (dd, J=13.2, 8.5 Hz, 1H), 1.93-1.87 (m, 1H), 1.82 (br s, 1H), 1.69-1.62 (m, 1H), 1.49-1.41 (m, 1H), 1.39-1.32 (m, 1H), 0.75 (s, 9H), −0.12 (s, 3H), −0.27 (s, 3H). LC-MS: m/z (ES) 462.5 (MH)$^+$.

Intermediate 8

Tert-butyl(2S,5R)-2-(4-aminobenzyl)-5-[(R)-{[tert-butyl(dimethyl)silyl]oxy}(pyridin-3-yl)methyl]pyrrolidine-1-carboxylate (i-8)

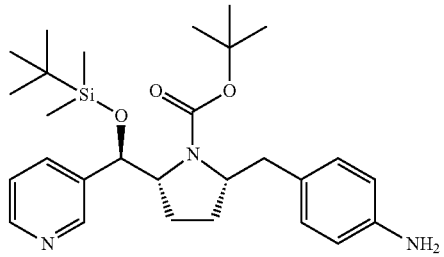 [SMILES: CC(C)(C)OC(=O)N1[C@H](Cc2ccc(N)cc2)CC[C@@H]1[C@H](O[Si](C)(C)C(C)(C)C)c1cccnc1]

Step A: Tert-butyl(2R,5S)-2-[(R){[tert-butyl(dimethyl)silyl]oxy}(6-chloropyridin-3-yl)methyl]-5-(4-nitrobenzyl)pyrrolidine-1-carboxylate To a stirred solution of 6.5 g (14 mmol) of Intermediate 6 in 100 mL of anhydrous dichloromethane at ambient temperature under an atmosphere of nitrogen was added 4.9 mL (21 mmol) of diisopropylethylamine followed by 3.6 g (28 mmol) of di-tart-butyl Bicarbonate and the resulting mixture was stirred for 4 h. The reaction mixture was evaporated to dryness in vacuo and the crude residue purified by silica gel chromatography eluting with a 5-10% ethyl acetate in hexanes gradient to afford the title compound as a colorless gum (6.4 g, 81%). LC-MS: m/z (ES) 562.3 (MH)$^+$.

Step B: Tert-butyl(2S,5R)-2-(4-aminobenzyl)-5-[(R)-{[tert-butyl(dimethyl)silyl]oxy}-(pyridine-3-yl)methyl]pyrrolidine-1-carboxylate To 0.70 g (0.66 mmol) of 10% palladium on carbon was added a solution of 6.4 g (11 mmol) of tert-butyl(2R,5S)-2-[(R)-{[tert-butyl(dimethyl)silyl]oxy}(6-chloropyridin-3-yl)methyl]-5-(4-nitrobenzyl)pyrrolidine-1-carboxylate from Step A above in 75 mL of anhydrous ethanol followed by 1.2 g (12 mmol) of potassium acetate. The resulting suspension was agitated under an atmosphere of hydrogen at 50 psi for 8 h. then filtered through a plug of Celite®. The plug was washed with ethanol (100 mL) and the combined filtrates were concentrated in vacuo. The residue was purified by silica gel chromatography eluting with 40% ethyl acetate in hexanes to afford the title compound (i-8) as a colorless solid (0.31 g, 76%). LC-MS: m/z (ES) 498.4 (MH)$^+$.

Intermediate 9

Tert-butyl(2R,5S)-2-[(R)-{[tert-butyl(dimethyl)silyl]oxy}(phenyl)methyl]-5-(3,4-diaminobenzyl)pyrrolidine-1-carboxylate (i-9)

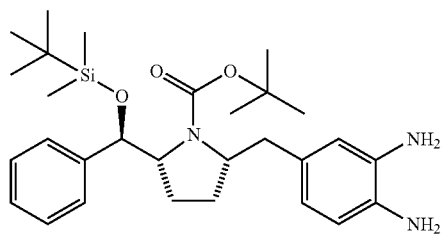

Step A: Tert-butyl(2S,5R)-2-(4-amino-3-nitrobenzyl)-5-[(R)-{[tertbutyl(dimethyl)silyl]oxy}(phenyl)methyl]pyrrolidine-1-carboxylate

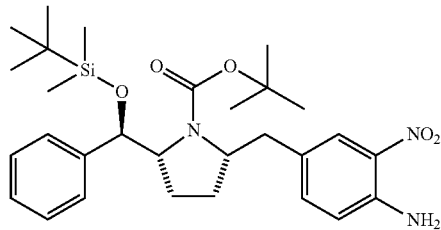

To a stirred solution of 2.67 g (5.37 mmol) of Intermediate 4a (i-4a) in 8 mL of glacial acetic acid under an atmosphere of nitrogen cooled to 0° C. was added 2.65 g (5.64 mmol) of 2,3,5,6-tetrabromo-4-methyl-4-nitrocyclohexa-2,5-dien-1-one in one portion. The resulting reaction mixture was allowed to stir for two hours then quenched by slowly pouring over 200 mL of a 10% aqueous sodium bicarbonate solution. The aqueous phase was then extracted with dichloromethane (3×25 mL) and washed with 100 mL water. The combined organic layers were dried over magnesium sulfate, filtered and evaporated in vacuo. The crude residue was purified by silica gel chromatography eluting with a 30% ethyl acetate in hexanes mixture to afford the title compound as a yellow gum. LC/MS: m/z (ES) 564.4 (MNa)$^+$.

Step B: Tert-butyl(2R,5S)-2-[(R)-{[tert-butyl(dimethyl)silyl]oxy}(phenyl)methyl]-5-(3,4-diaminobenzyl)pyrrolidine-1-carboxylate

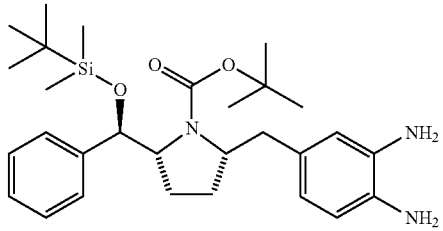

To a solution of 0.58 g (1.1 mmol) of tert-butyl(2S,5R)-2-(4-amino-3-nitrobenzyl)-5-[(R)-{[tertbutyl(dimethyl)silyl]oxy}(phenyl)methyl]pyrrolidine-1-carboxylate from Step A in 5 mL of acetic acid was added 0.35 g (5.4 mmol) of zinc dust and the resulting mixture was stirred under nitrogen for 1 h. The reaction mixture was then filtered through a pad of Celite. The pad was washed with dichloromethane (3×25 mL) and the combined filtrates were concentrated in vacuo. The crude residue was purified by reverse-phase HPLC (TMC Pro-Pac C18; 10-100% 0.1% trifluoroacetic acid in acetonitrile/0.1% trifluoroacetic acid in water gradient) to afford the title compound as a yellow solid. LC/MS: m/z (ES) 512.3 (MH)$^+$.

Intermediate 10

Tert-butyl(2R,5S)-2-[(R){[tert-butyl(dimethyl)silyl]oxy}(pyridin-3-yl)methyl]-5-(3,4-diaminobenzyl)pyrrolidine-1-carboxylate (i-10)

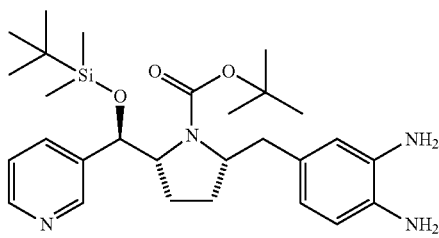

Intermediate 10 (i-10) was prepared from Intermediate 8 (i-8) according to the same procedures outlined for the synthesis of Intermediate 9.

Biological Assays:

The following in vitro assays are suitable for screening compounds that have selective β3 agonist activity:

Functional Assay:

cAMP production in response to ligand is measured according to Barton, et al. (1991, Agonist-induced desensitization of D2 dopamine receptors in human Y-79 retinoblastoma cells. Mal. Pharmacol. v3229:650-658) modified as follows. cAMP production is measured using a homogenous time-resolved fluorescence resonance energy transfer immunoassay (LANCE™, Perkin Elmer) according to the manufacture's instructions. Chinese hamster ovary (CHO) cells, stably transfected with the cloned β-adrenergic receptor (β1, β2 or β3) are harvested after 3 days of subculturing. Harvesting of cells is done with Enzyme-free Dissociation. Media (Specialty Media). Cells are then counted and resuspended in assay buffer (Hank's Balanced salt solution supplemented with 5 mM HEPES, 0.1% BSA) containing a phosphodiesterase inhibitor (IBMX, 0.6 mM). The reaction is initiated by mixing 6,000 cells in 6 μL with 6 μL Alexa Fluor labeled cAMP antibody (LANCE™ kit) which is then added to an assay well containing 12 μL of compound (diluted in assay buffer to 2x final concentration). The reaction proceeds for 30 min at room temperature and is terminated by the addition of 24 μL detection buffer (LANCE™ kit). The assay plate is then incubated for 1 h at room temperature and time-resolved fluorescence measured on a Perkin Elmer Envision reader or equivalent. The unknown cAMP level is determined by comparing fluorescence levels to a cAMP standard curve.

The non-selective, full agonist β-adrenergic ligand isoproterenol is used at all three receptors to determine maximal stimulation. The human β3 adrenergic receptor (AR) selective ligand (S)—N-[4-[2-[[2-hydroxy-3-(4-hydroxyphenoxy)propyl]amino]ethyl]-phenyl]-4-iodobenzenesulfonamide is used as a control in all assays. Isoproterenol is titrated at a final concentration in the assay of 10-10 M to 10-5 and the selective ligand (S)—N-[4-[2-[[2-hydroxy-3-(4-hydroxyphenoxy)propyl]amino]ethyl]phenyl]-4-iodobenzenesulfonamide is titrated at the β3 receptor at concentration of 10-10 M to 10-5 M. Unknown ligands are titrated at all 3 β-adrenergic receptor subtypes at a final concentration in the assay of 10-10 M to 10-5 M to determine the $EC_{50}$. The $EC_{50}$ is defined as the concentration of compound that gives 50% activation of its own maximum. Data are analyzed using Microsoft Excel and Graphpad Prism or an internally developed data analysis software package.

Binding Assay:

Compounds are also assayed at the β1 and β2 receptors to determine selectivity. All binding assays are run using membranes prepared from CHO cells recombinantly expressing β1 or β2 receptors. Cells are grown for 3-4 days post splitting; the attached cells are washed with PBS and then lysed in 1 mM Tris, pH 7.2 for 10 min on ice. The flasks are scraped to remove the cells and the cells then homogenized using a Teflon/glass homogenizer. Membranes are collected by centrifuging at 35,000×g for 15 min at 4° C. The pelleted membranes are resuspended in TME buffer (50 mM Tris, pH 7.4, 5 mM $MgCl_2$, 2 mM EDTA) at a concentration of 1 mg protein/mL. Large batches of membranes can be prepared, aliquoted and stored at −70° C. for up to a year without loss of potency. The binding assay is performed by incubating together membranes (2-5 μg of protein), the radiolabelled tracer $^{125}$I-cyanopindolol ($^{125}$I-CYP, 45 pM), 200 μg of WGA-PVT SPA beads (GE Healthcare) and the test compounds at final concentrations ranging from 10-10 M to 10-5 M in a final volume of 200 μL of TME buffer containing 0.1% BSA. The assay plate is incubated for 1 h with shaking at room temperature and then placed in a Perkin Elmer Trilux scintillation counter. The plates are allowed to rest in the Trilux counter for approximately 10 h in the dark prior to counting. Data are analyzed using a standard 4-parameter non-linear regression analysis using either Graphpad Prism software or an internally developed data analysis package. The $IC_{50}$ is defined as the concentration of the compound capable of inhibiting 50% of the binding of the radiolabelled tracer ($^{125}$I-CYP). A compound's selectivity for the β3 receptor may be determined by calculating the ratio ($IC_{50}$ β1 AR, β2 AR)/($EC_{50}$ β3 AR).

The following examples are provided to illustrate the invention and are not to be construed as limiting the scope of the invention in any manner.

Example 1

1-{(1S)-[6-({(2S,5R)-5-[(R)-Hydroxy(phenyl)methyl]pyrrolidin-2-yl}methyl)-1H-benzimidazol-2-yl]ethyl}pyrimidin-2(1H)-one

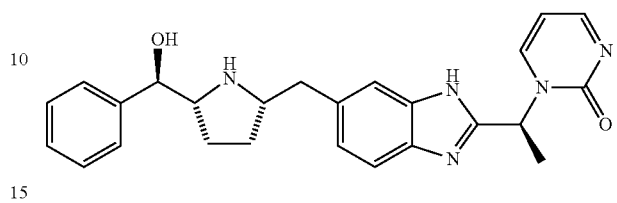

Step A: Tert-butyl(2S,5R)-2-(3-amino-4-{[(2S)-2-(2-oxopyrimidin-1(2H)-yl)propanoyl]amino}benzyl)-5-[(R)-{[tert-butyl(dimethyl)silyl]oxy}(phenyl)methyl]pyrrolidine-1-carboxylate

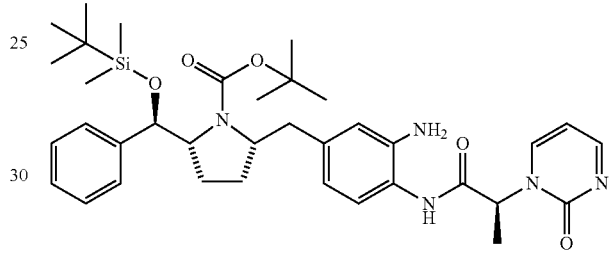

To a solution of 0.038 g (0.074 mmol) of Intermediate 9 in 5 ml of anhydrous N,N-dimethylformamide was added 0.013 g (0.074 mmol) of (2S)-2-(2-oxopyrimidin-1(2H)-yl) propanoic acid, 0.15 mL (0.089 mmol) of HOAt followed by 0.017 g (0.089 mmol) of EDC. The resulting mixture was stirred under an atmosphere of nitrogen overnight and then diluted with 10 mL of a saturated aqueous sodium bicarbonate solution. The aqueous solution was extracted with ethyl acetate (3×10 mL) and the combined organic layers were dried over magnesium sulfate, filtered and evaporated in vacuo. The crude material was purified by reverse-phase chromatography (TMC Pro-Pac C18; 10-100% 0.1% trifluoroacetic acid in acetonitrile/0.1% trifluoroacetic acid in water gradient) to afford the title compound as a white solid. LC/MS: m/z (ES) 548.5 (MH)⁺.

Step B: Tert-butyl(2R,5S)-2-[(R)-{[tert-butyl(dimethyl)silyl]oxy}(phenyl)methyl]-5-({2-[(1S)-1-(2-oxopyrimidin-1(2H)-yl)ethyl]-1H-benzimidazol-6-yl}methyl)pyrrolidine-1-carboxylate

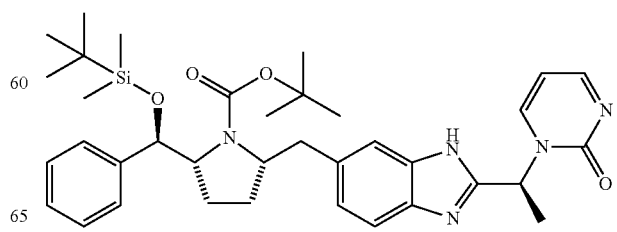

A solution of 0.020 g (0.030 mmol) of tert-butyl(2S,5R)-2-(3-amino-4-{[(2.5)-2-(2-oxopyrimidin-1(2H)-yl)propanoyl]amino}benzyl)-5-[(R)-{[tert-butyl(dimethyl)silyl]oxy}(phenyl)methyl]pyrrolidine-1-carboxylate from Step A above in 1 mL of glacial acetic acid under an atmosphere of nitrogen was heated to 100° C. for 1 h. The resulting solution was allowed to cool to ambient temperature and then concentrated in vacuo to afford the title compound as a light brown gum that was used without further purification. LC/MS: m/z (ES) 644.5 (MH)+.

Step C: 1-{(1S)-1-[6-({(2S,5R)-5-[(R)-Hydroxy(phenyl)methyl]pyrrolidin-2-yl}methyl)-1H-benzimidazol-2-yl]ethyl}pyrimidin-2(1H)-one

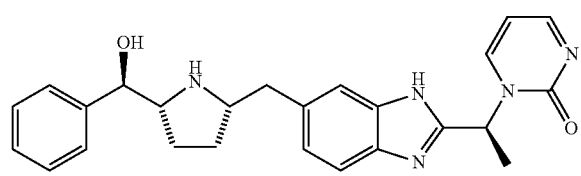

A solution of 0.017 g (0.026 mmol) of tert-butyl(2R,5S)-2-[(R)-{[tert-butyl(dimethyl)silyl]oxy}(phenyl)methyl]-5-({2-[(1S)-1-(2-oxopyrimidin-1(2H)-yl)ethyl]-1H-benzimidazo-6-yl}methyl)pyrrolidine-1-carboxylate from Step B above in 2 mL of a 3:3:1 trifluoroacetic acid:acetonitrile:water mixture was stirred at 70° C. for 3 h. All volatiles were removed in vacuo and the crude light brown residue was purified by reverse-phase HPLC (TMC Pro-Pac C18; 10-100% 0.1% trifluoroacetic acid in acetonitrile/0.1% trifluoroacetic acid in water gradient) to afford the title compound as a white solid. $^1$H-NMR (500 MHz, CD$_3$OD) δ 8.85-8.62 (m, 1H), 8.57-8.31 (m, 1H), 7.91-7.65 (m, 2H), 7.64-7.24 (m, 9H), 6.86-6.59 (m, 1H), 6.19-5.87 (m, 1H), 4.85-4.67 (m, 2H), 4.04-3.68 (m, 4H), 3.28-3.10 (m, 2H), 2.30-1.62 (m, 4H). LC/MS: m/z (ES) 430.2 (MH)+.

Following similar procedures as outlined in Example 1, the Examples listed in Table 1 were prepared from Intermediates 9 and 10.

Using the Biological Assays as described above, the human β3 functional activity of each compound was determined and shown in Table 1 as the following ranges:

11-100 nM (+++);
101-1000 nM (++++); and
greater than 1000 nM but less than 3000 nM (+++++).

TABLE 1

| Example Number | U | R | MW | MS (MH)+ | Human β3 agonist functional activity |
|---|---|---|---|---|---|
| 1 | CH | (S)-1-(2-oxopyrimidin-1(2H)-yl)ethyl | 429.5 | 430.2 | +++ |
| 2 | CH | 2-(1H-pyrazol-1-yl)ethyl | 401.5 | 402.2 | ++++ |
| 3 | CH | 2-(pyrazin-2-yl)ethyl | 413.5 | 414.2 | ++++ |
| 4 | CH | 2-(1H-imidazol-1-yl)ethyl | 401.5 | 402.2 | ++++ |

TABLE 1-continued

| Example Number | U | R | MW | MS (MH)+ | Human β3 agonist functional activity |
|---|---|---|---|---|---|
| 5 | CH | (2-ethyl-benzimidazol-1-yl-propyl) | 479.6 | 480.3 | ++++ |
| 6 | CH | (pyrazol-1-yl-butyl) | 415.6 | 416.2 | ++++ |
| 7 | CH | (indazol-1-yl-propyl) | 451.6 | 452.2 | +++ |
| 8 | CH | (2-methyl-thiazol-4-yl-ethyl) | 418.6 | 419.2 | ++++ |
| 9 | CH | (indazol-1-yl-ethyl) | 437.6 | 438.2 | ++++ |
| 10 | CH | (2-phenyl-imidazol-1-yl-propyl) | 477.6 | 478.2 | ++++ |

TABLE 1-continued
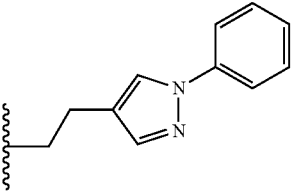 [SMILES: *CCc1cnn(-c2ccccc2)c1]
| Example Number | U | R | MW | MS (MH)+ | Human β3 agonist functional activity |
|---|---|---|---|---|---|
| 11 | CH | 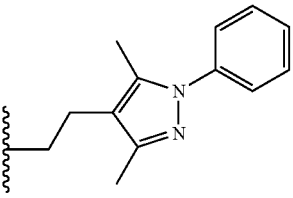 [SMILES: *CCc1c(C)nn(-c2ccccc2)c1C] | 477.6 | 478.2 | ++++ |
| 12 | CH | 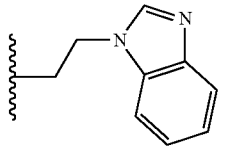 [SMILES: *CCn1cnc2ccccc21] | 505.7 | 506.2 | ++++ |
| 13 | CH | 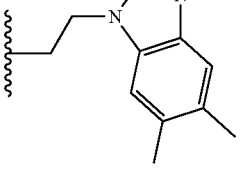 | 451.6 | 452.3 | ++++ |
| 14 | CH | 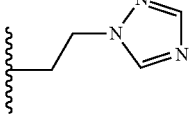 | 479.6 | 480.2 | ++++ |
| 15 | CH | 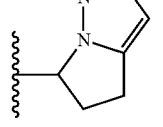 | 402.5 | 403.1 | ++++ |
| 16 | CH | 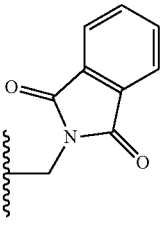 [SMILES: *CN1C(=O)c2ccccc2C1=O] | 413.5 | 414.4 | ++++ |
| 17 | CH |  | 466.6 | 467.2 | ++++ |

TABLE 1-continued

| Example Number | U | R | MW | MS (MH)+ | Human β3 agonist functional activity |
|---|---|---|---|---|---|
| 18 | CH | pyrazol-1-ylmethyl | 387.5 | 388.1 | ++++ |
| 19 | CH | (4-oxopyrimidin-3(4H)-yl)methyl | 415.5 | 416.1 | ++++ |
| 20 | CH | (2,5-dimethylthiazol-4-yl)methyl | 432.6 | 433.2 | ++++ |
| 21 | CH | 2-methyl-5,6-dihydro-4H-cyclopenta[d]thiazol-5-yl | 444.6 | 445.1 | +++ |
| 22 | CH | 1-(thiazol-4-yl)ethyl | 418.6 | 419.1 | +++ |
| 23 | CH | (1S)-1-(4-oxopyrimidin-3(4H)-yl)ethyl | 429.5 | 430.3 | ++++ |
| 24 | CH | 5,6-dihydro-4H-cyclopenta[d]thiazol-5-yl | 430.6 | 431.0 | +++ |

TABLE 1-continued

| Example Number | U | R | MW | MS (MH)+ | Human β3 agonist functional activity |
|---|---|---|---|---|---|
| 25a Isomer 1 | CH | 2-methyl-4,5,6,7-tetrahydrobenzothiazol-4-yl | 458.6 | 459.2 | ++++ |
| 25b Isomer 2 | CH | 2-methyl-4,5,6,7-tetrahydrobenzothiazol-4-yl | 458.6 | 459.2 | ++++ |
| 26 | N | 5,6-dihydro-4H-cyclopenta[d]thiazol-4-yl | 431.6 | 432.0 | ++++ |
| 27 | N | 1-(thiazol-4-yl)ethyl | 419.6 | 420.2 | ++++ |
| 28 | N | 1-(2-oxopyrimidin-1(2H)-yl)ethyl | 430.5 | 431.1 | ++++ |
| 29 | N | 2-methyl-5,6-dihydro-4H-cyclopenta[d]thiazol-4-yl | 445.6 | 446.0 | ++++ |
| 30 | N | 2-(1H-indazol-1-yl)ethyl | 452.6 | 453.2 | +++ |

TABLE 1-continued

| Example Number | U | R | MW | MS (MH)+ | Human β3 agonist functional activity |
|---|---|---|---|---|---|
| 31 | N | (2-(phthalimido)ethyl) | 467.5 | 468.0 | ++++ |
| 32 | N | (2-(methylsulfonyl)phenyl) | 462.6 | 463.0 | +++ |
| 33 | N | (4-(methylsulfonyl)phenyl) | 462.6 | 463.0 | ++++ |
| 34 | N | (3-(methylsulfonyl)phenyl) | 462.6 | 463.1 | +++ |
| 35 | N | (2-carboxyphenyl) | 428.5 | 429.0 | ++++ |
| 36 | N | (3-carboxyphenyl) | 428.5 | 429.0 | ++++ |

TABLE 1-continued

| Example Number | U | R | MW | MS (MH)+ | Human β3 agonist functional activity |
|---|---|---|---|---|---|
| 37 | N | 4-carboxyphenyl | 428.5 | 429.0 | +++ |
| 38 | N | 2,6-difluorophenyl | 420.5 | 421.0 | ++++ |
| 39 | N | 2-(trifluoromethyl)phenyl | 452.5 | 453.2 | +++ |
| 40 | N | 6-hydroxypyridin-2-yl | 401.5 | 402.6 | +++++ |
| 41 | N | 2-(imidazol-2-yl)phenyl | 450.6 | 451.1 | ++++ |
| 42 | N | 6,7-dihydro-5H-pyrrolo[1,2-a]pyrazol-? | 414.5 | 415.1 | ++++ |

Examples 43-46

Examples 43 and 44

(R)-[(2R,5S)-5-({1-methyl-2-[(4R and 4S)-2-methyl-5,6-dihydro-4H-cyclopenta[d][1,3]thiazol-4-yl]-1H-benzimidazol-6-yl}methyl)pyrrolidin-2-yl](phenyl)methanol and

Examples 45 and 46

(R)-[(2R,5S)-5-({1-methyl-2-[(4R and 4S)-2-methyl-5,6-dihydro-4H-cyclopenta[d][1,3]thiazol-4-yl]-1H-benzimidazol-5-yl}methyl)pyrrolidin-2-yl](phenyl)methanol Step A: Tert-butyl(2R,5S)-2-[(R)-{[tert-butyl(dimethyl)silyl]oxy}(phenyl)methyl]-5-{[2-(2-methyl-5,6-dihydro-4H-cyclopenta[d][1,3]thiazol-4-yl)-1H-benzimidazol-6-yl]methyl}pyrrolidine-1-carboxylate

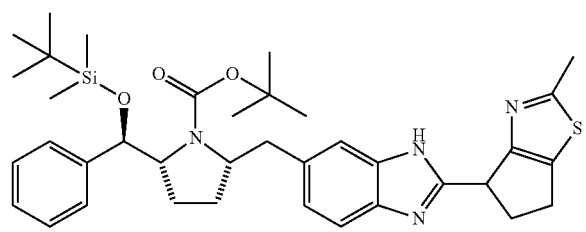

The title compound tert-butyl(2R,5S)-2-[(R)-{[tert-butyl(dimethyl)silyl]oxy}(phenyl)methyl]-5-{[2-(2-methyl-5,6-dihydro-4H-cyclopenta[d][1,3]thiazol-4-yl)-1H-benzimidazol-6-yl]methyl}pyrrolidine-1-carboxylate was prepared from Intermediate 3 and 2-methyl-5,6-dihydro-4H-cyclopenta[d][1,3]thiazole-4-carboxylic acid according to the procedures outlined in steps A and B for the preparation of Example 1. LC/MS: m/z (ES) 659.2 (MH)$^+$.

Step B: Tert-butyl(2R,5S)-2-[(R)-{[tert-butyl(dimethyl)silyl]oxy}(phenyl)methyl]-5-({1-methyl-2-[(4R and 4S)-2-methyl-5,6-dihydro-4H-cyclopenta[d][1,3]thiazol-4-yl]-1H-benzimidazol-6-yl}methyl)pyrrolidine-1-carboxylate and tert-butyl(2R,5S)-2-[(R)-{[tert-butyl(dimethyl)silyl]oxy}(phenyl)methyl]-5-({1-methyl-2-[(4R and 4S)-2-methyl-5,6-dihydro-4H-cyclopenta[d][1,3]thiazol-4-yl]-1H-benzimidazol-5-yl}methyl)pyrrolidine-1-carboxylate

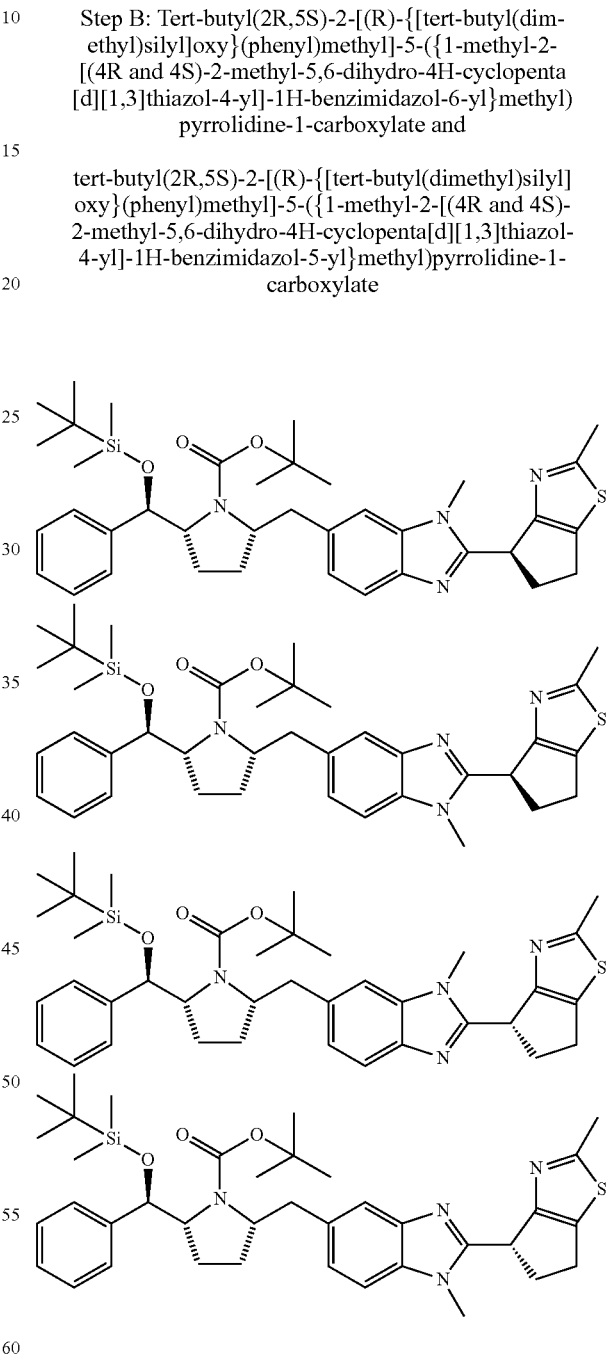

To a suspension of 0.003 g (0.07 mmol) of a 60% suspension of sodium hydride in mineral oil in 5 mL of anhydrous N,N-dimethylformamide cooled to 0° C. under an atmosphere of nitrogen was added 0.036 g (0.055 mmol) of tert-butyl(2R,5S)-2-[(R)-{[tert-butyl(dimethyl)silyl]oxy}(phenyl)methyl]-5-{[2-(2-methyl-5,6-dihydro-4H-cyclopenta[d][1,3]thiazol-4-yl)-1H-benzimidazol-6-yl]

methyl}pyrrolidine-1-carboxylate from Step A above. The resulting mixture was allowed to warm to ambient temperature and then 0.009 g (0.07 mmol) of methyl iodide was added. The reaction mixture was stirred for 3 h, quenched with water then extracted with ethyl acetate (3×10 mL). The combined organic layers were dried over magnesium sulfate, filtered and evaporated in vacuo. The resulting mixture of 4 compounds was separated by chiral HPLC employing a PREP CHIRALPAK® OD® column eluting with a 5% IPA in heptane mixture to afford the title compounds. The first isomer to elute was designated as Isomer 1, the second isomer as Isomer 2, the third as Isomer 3 and the fourth as Isomer 4.

Isomer 1 LC/MS: m/z (ES) 673.4 (MH)$^+$.
Isomer 2 LC/MS: m/z (ES) 673.4 (MH)$^+$.
Isomer 3 LC/MS: m/z (ES) 673.4 (MH)$^+$.
Isomer 4 LC/MS: m/z (ES) 673.4 (MH)$^+$.

Step C: Isomer 1 and 2: (R)-[(2R,5S)-5-({1-methyl-2-[(4R and 4S)-2-methyl-5,6-dihydro-4H-cyclopenta[d][1,3]thiazol-4-yl]-1H-benzimidazol-6-yl}methyl)pyrrolidin-2-yl](phenyl)methanol

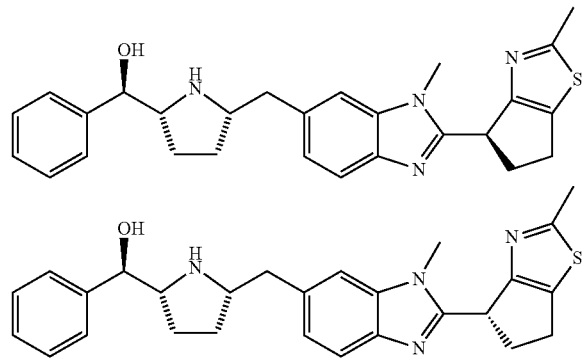

A stirred solution of 0.005 g (0.007 mmol) of Isomer 1 from Step B above in 2 mL of a 3:3:1 trifluoroacetic acid:acetonitrile:water mixture was stirred at 70° C. for 3 h. All volatiles were removed in vacuo and the crude light brown residue was purified by reverse-phase HPLC (TMC Pro-Pac C18; 10-100% 0.1% trifluoroacetic acid in acetonitrile/0.1% trifluoroacetic acid in water gradient) to afford the title compound as a white solid.

The same procedure outlined for Isomer 1 in Step C was applied to Isomer 2 of Step B to afford the title compound as a white solid.

Step D: Isomer 3 and 4: (R)-[(2R,5S)-5-({1-methyl-2-[(4R and 4S)-2-methyl-5,6-dihydro-4H-cyclopenta[d][1,3]thiazol-4-yl]-1H-benzimidazol-5-yl}methyl)pyrrolidin-2-yl](phenyl)methanol

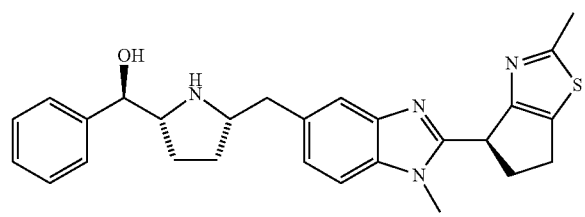 [SMILES: Cc1nc2c(s1)CCC2c1nc2cc(C[C@@H]3CC[C@H]([C@H](O)c4ccccc4)N3)ccc2n1C]

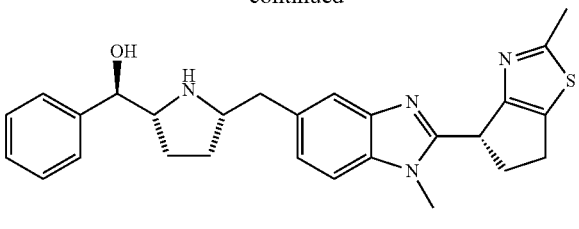

The same procedure outlined for Isomer 1 in Step C was applied to Isomer 3 and Isomer 4 of Step B to afford the title compounds as white solids.

Using the Biological Assays as described above, the human β3 functional activity of each compound was determined and shown in Tables 2 and 3 as the following ranges:

101-1000 nM (++++); and
greater than 1000 nM but less than 3000 nM (+++++).

TABLE 2

| Example | Isomer | MW | MS (MH)$^+$ | Human β3 agonist functional activity |
|---|---|---|---|---|
| 43 | 1 | 458.6 | 459.1 | +++++ |
| 44 | 2 | 458.6 | 459.1 | +++++ |

TABLE 3

| Example | Isomer | MW | MS (MH)$^+$ | Human β3 agonist functional activity |
|---|---|---|---|---|
| 45 | 3 | 458.6 | 459.2 | ++++ |
| 46 | 4 | 458.6 | 459.1 | +++++ |

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I, or a pharmaceutically acceptable salt thereof, or a stereoisomer thereof, or a pharmaceutically acceptable salt of the stereoisomer thereof:

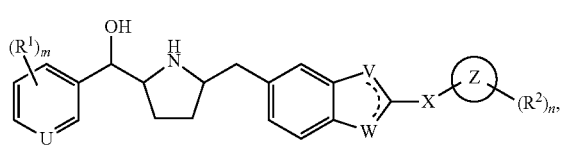

(I)

wherein
the dash bond "----" means a single or double bond while conforming to the valency rule for the ring atoms;
m is 0, 1, 2 or 3;
n is 0, 1, 2, 3 or 4;
p is 0, 1 or 2;
U is —CH= or —N=;
V is selected from the group consisting of:
  (1) —O—,
  (2) —N=, and
  (3) —NR$^3$—;
W is —N= or —NR$^3$—;
X is selected from the group consisting of:
  (1) a bond, and
  (2) $C_1$-$C_4$ alkanediyl optionally substituted with 1 to 3 groups independently selected from:
    (a) hydroxy,
    (b) halogen,
    (c) —CO$_2$R$^3$,
    (d) —CONR$^3$R$^3$, and
    (e) —NR$^3$R$^3$;
Z is selected from the group consisting of:
  (1) phenyl,
  (2) 5 or 6-membered heterocyclic ring with from 1 to 4 heteroatoms independently selected from oxygen, sulfur and nitrogen,
  (3) a $C_5$-$C_8$ carbocyclic ring fused to a 5 or 6-membered heterocyclic ring with from 1 to 4 heteroatoms independently selected from oxygen, sulfur and nitrogen, and
  (4) 5 or 6-membered heterocyclic ring with from 1 to 4 heteroatoms independently selected from oxygen, sulfur and nitrogen fused to a 5 or 6-membered heterocyclic ring with from 1 to 4 heteroatoms independently selected from oxygen, sulfur and nitrogen;
each occurrence of R$^1$ is independently selected from the group consisting of:
  (1) $C_1$-$C_4$ alkyl optionally substituted with 1 to 3 groups independently selected from:
    (a) hydroxy,
    (b) halogen, and
    (c) $C_3$-$C_8$ cycloalkyl;
  (2) $C_3$-$C_8$ cycloalkyl,
  (3) oxo, and
  (4) halogen;
each occurrence of R$^2$ is independently selected from the group consisting of:
  (1) hydroxy,
  (2) halogen,
  (3) oxo,
  (4) —CO$_2$R$^3$,
  (5) $C_3$-$C_8$ cycloalkyl,
  (6) —S(O)$_p$—$C_1$-$C_4$ alkyl,
  (7) $C_1$-$C_4$ alkyl optionally substituted with 1 to 3 groups independently selected from
    (a) hydroxy,
    (b) halogen,
    (c) —CO$_2$R$^3$,
    (d) —S(O)$_p$—$C_1$-$C_4$ alkyl,
    (e) $C_3$-$C_8$ cycloalkyl, and
    (f) Z optionally substituted with 1 to 4 groups independently selected from hydroxyl, halogen, oxo, trifluoromethyl, trifluoromethoxy, $C_1$-$C_4$ alkyl, $C_1$-$C_4$ alkoxy, and —CO$_2$R$^3$, and
  (8) Z optionally substituted with 1 to 4 groups independently selected from hydroxyl, halogen, oxo, trifluoromethyl, trifluoromethoxy, $C_1$-$C_4$ alkyl, $C_1$-$C_4$ alkoxy, —SO$_2$—CH$_3$, and —CO$_2$R$^3$; and
each occurrence of R$^3$ is independently selected from the group consisting of:
  (1) hydrogen, and
  (2) $C_1$-$C_4$ alkyl optionally substituted with 1 to 2 groups independently selected from phenyl, halogen, cyano and hydroxyl.

2. The compound of claim 1, wherein V is —NH— and W is —N=.

3. The compound of claim 2, wherein m is 0 and n is 0, 1, 2 or 3.

4. The compound of claim 3, wherein X is selected from the group consisting of:
  (1) a bond,
  (2) —CH$_2$—,
  (3) —CH$_2$CH$_2$—,
  (4) —CH(CH$_3$)—
  (5) —CH$_2$CH$_2$CH$_2$—, and
  (6) —CH(CH$_3$)CH$_2$—.

5. The compound of claim 3, wherein Z is selected from the group consisting of:
  (1) phenyl,
  (2) a 5-membered heterocyclic ring having 1 N ring atom and 0 to 2 additional hetero ring atoms independently selected from N, O and S,
  (3) a 6-membered heterocyclic ring having 1 N ring atom and 0 to 2 additional hetero ring atoms independently selected from N, O and S,
  (4) a $C_5$-$C_6$ carbocyclic ring fused to a 5-membered heterocyclic ring having 1 N ring atom and 0 to 2 additional hetero ring atoms independently selected from N, O and S,
  (5) a $C_5$-$C_6$ carbocyclic ring fused to a 6-membered heterocyclic ring having 1 N ring atom and 0 to 2 additional hetero ring atoms independently selected from N, O and S,
  (6) a 5-membered heterocyclic ring having 1 N ring atom and 0 to 2 additional hetero ring atoms independently selected from N, O and S fused to a 5-membered heterocyclic ring having 1 N ring atom and 0 to 2 additional hetero ring atoms independently selected from N, O and S,
  (7) a 5-membered heterocyclic ring having 1 N ring atom and 0 to 2 additional hetero ring atoms independently selected from N, O and S fused to a 6-membered heterocyclic ring having 1 N ring atom and 0 to 2 additional hetero ring atoms independently selected from N, O and S, and
  (8) a 6-membered heterocyclic ring having 1 N ring atom and 0 to 2 additional hetero ring atoms independently selected from N, O and S fused to a 6-membered heterocyclic ring having 1 N ring atom and 0 to 2 additional hetero ring atoms independently selected from N, O and S.

6. The compound of claim 5, wherein Z is selected from the group consisting of:
(1) phenyl,
(2) a 5-membered heterocyclic ring having 1 N ring atom and 0 to 2 additional hetero ring atoms independently selected from N, O and S,
(3) a 6-membered heterocyclic ring having 1 N ring atom and 0 to 2 additional hetero ring atoms independently selected from N, O and S,
(4) a $C_5$-$C_6$ carbocyclic ring fused to a 5-membered heterocyclic ring having 1 N ring atom and 0 to 2 additional hetero ring atoms independently selected from N, O and S,
(5) a 5-membered heterocyclic ring having 1 N ring atom and 0 to 2 additional hetero ring atoms independently selected from N, O and S fused to a 5-membered heterocyclic ring having 1 N ring atom and 0 to 2 additional hetero ring atoms independently selected from N, O and S, and
(6) a 5-membered heterocyclic ring having 1 N ring atom and 0 to 2 additional hetero ring atoms independently selected from N, O and S fused to a 6-membered heterocyclic ring having 1 N ring atom and 0 to 2 additional hetero ring atoms independently selected from N, O and S.

7. The compound of claim 6 wherein Z is selected from the group consisting of phenyl, thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,2,5-oxadiazolyl,

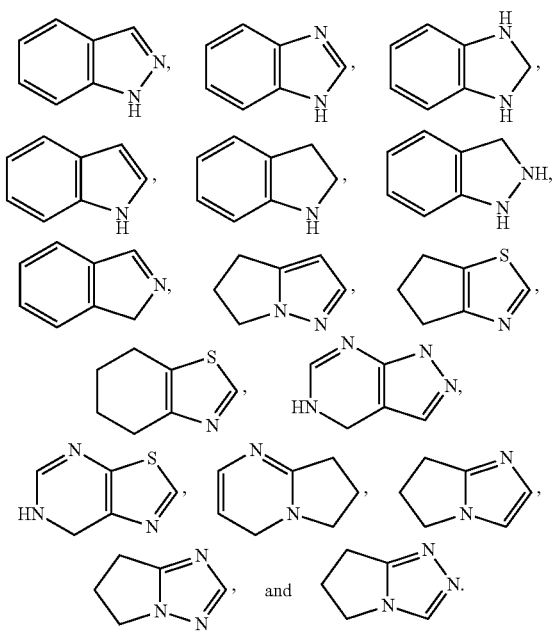

8. The compound of claim 6 wherein Z is selected from the group consisting of phenyl, thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,2,5-oxadiazolyl,

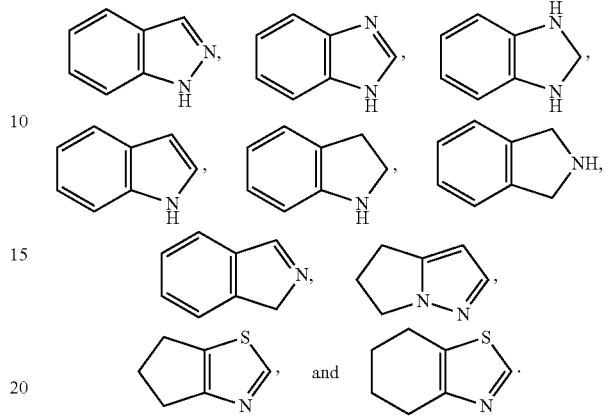

9. The compound of claim 1 wherein each occurrence of $R^2$ is independently selected from the group consisting of:
(1) hydroxy,
(2) fluoro,
(3) oxo,
(4) —$CO_2H$,
(5) methyl, ethyl or propyl, each of which optionally substituted with 1 to 2 groups independently selected from hydroxy and halogen,
(6) —$SO_2$—$CH_3$, and
(7) Z optionally substituted with 1 to 3 groups independently selected from hydroxyl, halogen, oxo, trifluoromethyl, trifluoromethoxy, methyl, ethyl, and —$CO_2H$.

10. The compound of claim 1 wherein each occurrence of $R^3$ is independently selected from the group consisting of:
(1) hydrogen,
(2) methyl, and
(3) ethyl.

11. A compound of Formula Ic, or a pharmaceutically acceptable salt thereof:

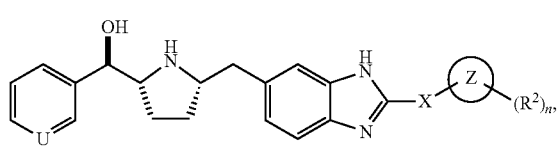

(Ic)

wherein
n is 0, 1, 2, 3 or 4;
U is —CH= or —N=;
X is selected from the group consisting of:
(1) a bond,
(2) —$CH_2$—,
(3) —$CH(CH_3)$—
(4) —$CH_2CH_2$—,
(5) —$CH(CH_3)CH_2$—, and
(6) —$CH_2CH_2CH_2$—;
Z is selected from the group consisting of:
(1) phenyl,
(2) a 5-membered heterocyclic ring having 1 N ring atom and 0 to 2 additional hetero ring atoms independently selected from N, O and S, (3) a 6-membered heterocyclic ring having 1 N ring atom and 0 to 2 additional hetero ring atoms independently selected from N, O and S, (4) a $C_5$-$C_6$ carbocyclic ring fused to a 5-membered heterocyclic ring having 1 N ring atom and 0 to 2 additional hetero ring atoms independently selected from N, O and S, (5) a 5-membered heterocyclic ring having 1 N ring atom and 0 to 2 additional hetero ring atoms independently selected from N, O and S fused to a 5-membered heterocyclic ring having 1 N ring atom and 0 to 2 additional hetero ring atoms independently selected from N, O and S, and (6) a 5-membered heterocyclic ring having 1 N ring atom and 0 to 2 additional hetero ring atoms independently selected from N, O and S fused to a 6-membered heterocyclic ring having 1 N ring atom and 0 to 2 additional hetero ring atoms independently selected from N, O and S;

each occurrence of $R^2$ is independently selected from the group consisting of:
(1) hydroxy,
(2) halogen,
(3) oxo,
(4) —$CO_2R^3$,
(5) —$SO_2R^3$,
(6) $C_1$-$C_4$ alkyl optionally substituted with 1 to 3 groups independently selected from
  (a) hydroxy,
  (b) halogen,
  (c) —$CO_2R^3$,
  (d) —$SO_2R^3$, and
  (e) Z optionally substituted with 1 to 4 groups independently selected from hydroxyl, halogen, oxo, trifluoromethyl, trifluoromethoxy, $C_1$-$C_4$ alkyl, $C_1$-$C_4$ alkoxy, and —$CO_2R^3$, and
(7) Z optionally substituted with 1 to 4 groups independently selected from hydroxyl, halogen, oxo, trifluoromethyl, trifluoromethoxy, $C_1$-$C_4$ alkyl, $C_1$-$C_4$ alkoxy, —$SO_2R^3$, and —$CO_2R^3$; and each occurrence of $R^3$ is independently selected from the group consisting of:
(1) hydrogen, and
(2) $C_1$-$C_4$ alkyl.

12. The compound of claim 11, wherein Z is selected from the group consisting of: phenyl, thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,2,5-oxadiazolyl,

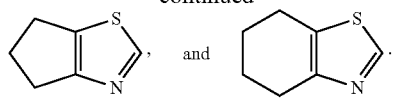

13. The compound of claim 11, wherein each occurrence of $R^2$ is independently selected from the group consisting of:
(1) hydroxy,
(2) halogen,
(3) oxo,
(4) —$CO_2H$,
(5) —$CO_2CH_3$,
(6) methyl, ethyl or propyl, each of which optionally substituted with 1 to 2 groups independently selected from hydroxy, halogen and Z optionally substituted with 1 to 4 groups independently selected from hydroxyl, halogen, oxo, trifluoromethyl, trifluoromethoxy, methyl, ethyl, —$CO_2H$, and —$CO_2CH_3$,
(7) —$SO_2$—$CH_3$, and
(8) Z optionally substituted with 1 to 4 groups independently selected from hydroxyl, halogen, oxo, trifluoromethyl, trifluoromethoxy, methyl, ethyl and —$CO_2H$.

14. The compound of claim 11, wherein each occurrence of $R^2$ is independently selected from the group consisting of:
(1) hydroxy,
(2) fluoro,
(3) oxo,
(4) —$CO_2H$,
(5) methyl or ethyl, each of which optionally substituted with 1 to 2 groups independently selected from hydroxy, halogen and Z optionally substituted with 1 to 3 groups independently selected from hydroxyl, halogen, oxo, trifluoromethyl, methyl, ethyl, and —$CO_2H$,
(6) —$SO_2$—$CH_3$, and
(7) Z optionally substituted with 1 to 3 groups independently selected from hydroxyl, halogen, oxo, trifluoromethyl, methyl, ethyl, and —$CO_2H$.

15. The compound of claim 1 selected from those listed in Tables 1, 2 and 3

TABLE 1

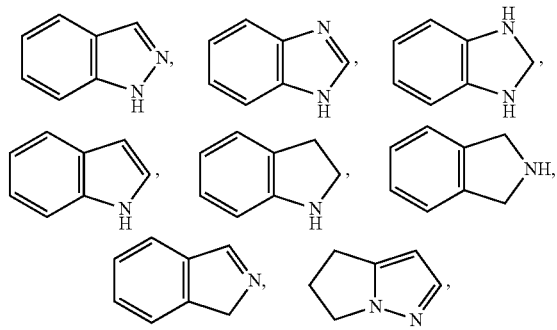

| Example Number | U | R |
|---|---|---|
| 1 | CH | |
| 2 | CH | |

TABLE 1-continued
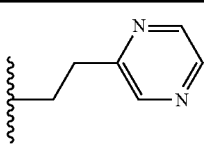
| Example Number | U | R |
|---|---|---|
| 3 | CH | 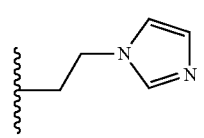 [SMILES: *CCn1ccnc1] |
| 4 | CH | 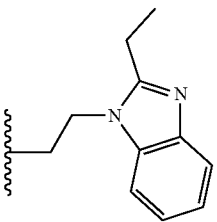 [SMILES: *CCn1c(CC)nc2ccccc21] |
| 5 | CH | 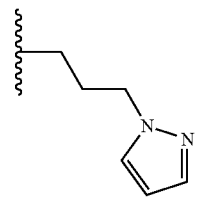 [SMILES: *CCCn1cccn1] |
| 6 | CH | 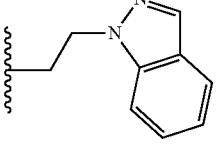 |
| 7 | CH | 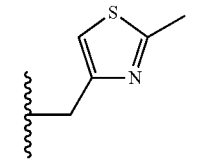 [SMILES: *Cc1csc(C)n1] |
| 8 | CH | 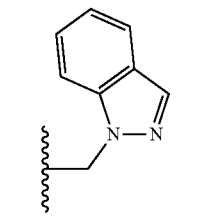 [SMILES: *Cn1ncc2ccccc21] |
| 9 | CH | 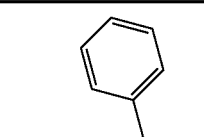 |
| 10 | CH | 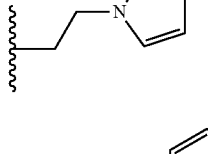 |
| 11 | CH | 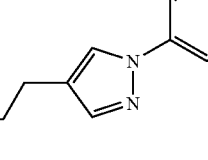 |
| 12 | CH | 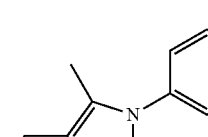 |
| 13 | CH | 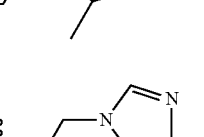 |
| 14 | CH | 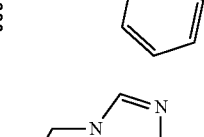 |
| 15 | CH | 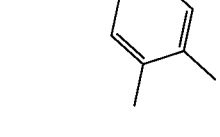 |
| 16 | CH | 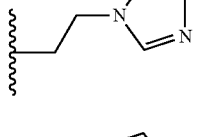 |

TABLE 1-continued
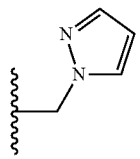 [SMILES: *Cn1cccn1]
| Example Number | U | R |
|---|---|---|
| 17 | CH | 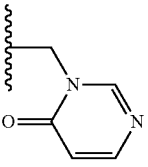 |
| 18 | CH | 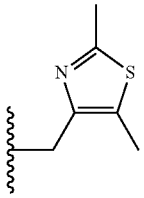 [SMILES: *Cc1nc(C)sc1C] |
| 19 | CH | 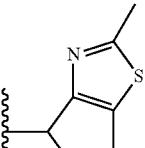 |
| 20 | CH | 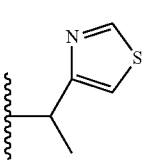 [SMILES: *C(C)c1cscn1] |
| 21 | CH | 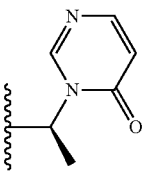 [SMILES: *[C@H](C)n1cnccc1=O] |
| 22 | CH | 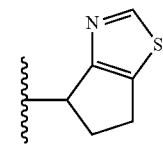 [SMILES: *C1CCc2scnc21] |
| 23 | CH | 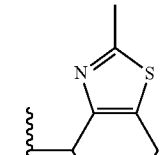 |
TABLE 1-continued
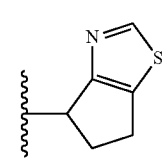 [SMILES: *C1CCc2scnc21]
| Example Number | U | R |
|---|---|---|
| 24 | CH | 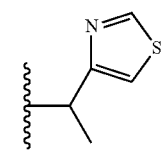 [SMILES: *C(C)c1cscn1] |
| 25a Isomer 1 | CH | 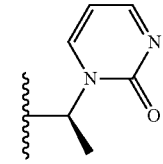 [SMILES: *[C@H](C)n1cccnc1=O] |
| 25b Isomer 2 | CH | 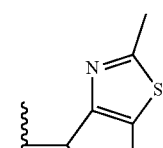 |
| 26 | N | |
| 27 | N | |
| 28 | N | |
| 29 | N | |

TABLE 1-continued
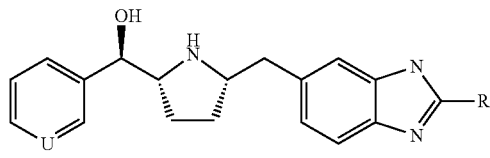
| Example Number | U | R |
|---|---|---|
| 30 | N | 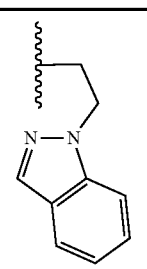 |
| 31 | N | 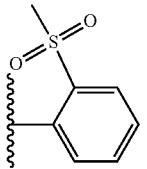 [SMILES: *c1ccccc1S(C)(=O)=O] |
| 32 | N | 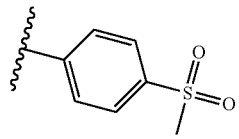 [SMILES: *c1ccc(S(C)(=O)=O)cc1] |
| 33 | N | 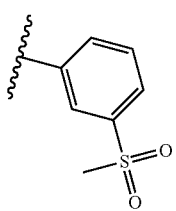 [SMILES: *c1cccc(S(C)(=O)=O)c1] |
| 34 | N | 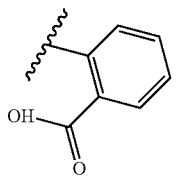 [SMILES: *c1ccccc1C(=O)O] |
| 35 | N | 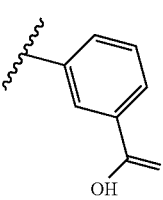 |
| 36 | N | 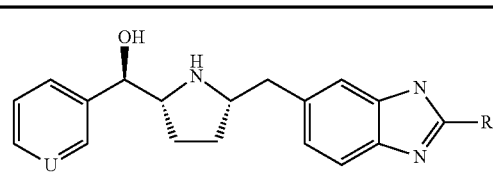 |
TABLE 1-continued
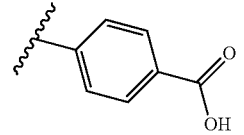 [SMILES: *c1ccc(C(=O)O)cc1]
| Example Number | U | R |
|---|---|---|
| 37 | N | 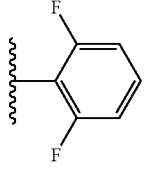 [SMILES: *c1c(F)cccc1F] |
| 38 | N | 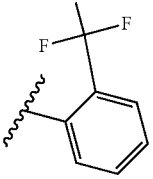 |
| 39 | N | 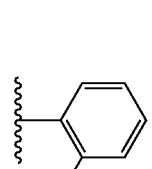 |
| 40 | N | 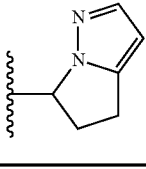 |
| 41 | N |  |
| 42 | N |  |

TABLE 2

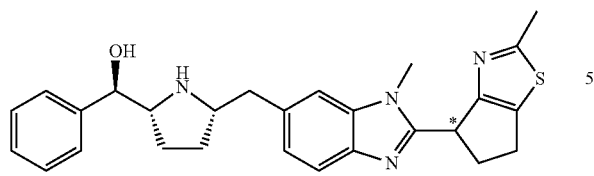

| Example | Isomer | MW | MS (MH)+ | Human β3 agonist functional activity |
|---|---|---|---|---|
| 43 | 1 | 458.6 | 459.1 | +++++ |
| 44 | 2 | 458.6 | 459.1 | +++++. |

16. A pharmaceutical composition comprising a compound of claim 1 and a pharmaceutically acceptable carrier.

17. A method for the treatment of a disease or disorder mediated by the activation of β3-adrenoceptor, wherein said method comprises administering to a patient in need thereof a therapeutically effective amount of a compound of claim 1.

18. The method of claim 17 wherein the disease or disorder is selected from the group consisting of (1) overactive bladder, (2) urinary incontinence, (3) urge urinary incontinence, and (4) urinary urgency.

19. A method for the treatment of a disease or disorder mediated by the activation of β3-adrenoceptor, wherein the method comprises administering to a patient in need thereof a therapeutically effective amount of a compound of claim 1 and a second active agent.

* * * * *